US008034340B2

(12) United States Patent
Wallach et al.

(10) Patent No.: US 8,034,340 B2
(45) Date of Patent: Oct. 11, 2011

(54) METHOD FOR TREATING AN IMMUNE DISORDER BY DECREASING NIK-SIVA COMPLEX FORMATION

(75) Inventors: David Wallach, Rehovot (IL); Parameswaran Ramakrishnan, Rehovot (IL); Wangxia Wang, Zhang Ping (CN); Taisia Shmushkovich, Rehovot (IL)

(73) Assignee: Yeda Research and Development Ltd., Rehovot (IL)

( * ) Notice: Subject to any disclaimer, the term of this patent is extended or adjusted under 35 U.S.C. 154(b) by 238 days.

(21) Appl. No.: 10/580,542

(22) PCT Filed: Nov. 30, 2004

(86) PCT No.: PCT/IL2004/001095
§ 371 (c)(1),
(2), (4) Date: Mar. 2, 2007

(87) PCT Pub. No.: WO2005/051423
PCT Pub. Date: Jun. 9, 2005

(65) Prior Publication Data
US 2008/0025968 A1 Jan. 31, 2008

(30) Foreign Application Priority Data

Nov. 30, 2003 (IL) .......................................... 159133
Jul. 28, 2004 (IL) .......................................... 163250

(51) Int. Cl.
*A61K 39/00* (2006.01)
*C07K 16/00* (2006.01)
*C07K 16/44* (2006.01)

(52) U.S. Cl. ................ 424/139.1; 530/387.1; 530/387.9

(58) Field of Classification Search ........................ None
See application file for complete search history.

(56) References Cited

U.S. PATENT DOCUMENTS

| | | | |
|---|---|---|---|
| 5,843,721 A | | 12/1998 | Rothe et al. |
| 6,010,853 A | * | 1/2000 | Kanteti et al. ................... 435/6 |
| 2003/0092044 A1 | * | 5/2003 | Goddard et al. ................ 435/6 |

FOREIGN PATENT DOCUMENTS

| | | | |
|---|---|---|---|
| IL | 03/087374 | * | 10/2003 |
| WO | 9737016 A1 | | 10/1997 |
| WO | 9854323 A1 | | 12/1998 |
| WO | 03087380 A1 | | 10/2003 |
| WO | 2005033142 A2 | | 4/2005 |

OTHER PUBLICATIONS

McEachern et al., BRCA1 splice variants exhibit overlapping and disctinct transcriptional transactivational activities. J Cell. Biochem., 89, 120-132, 2003.*
Joske DJL,Chronic myeloid leukaemia: the evolution of gene-targeted therapy. Med. J. Aust., 189,277-282, 2008.*
Richardson et al, Intrabody-mediated knockout of the high-affinity IL-2 receptor in primary human T cells using a bicistronic lentivirus vector. Gene therapy, 5, 635-644, 1998.*
Lo et al. Intracellular Antibodies (Intrabodies) and Their Therapeutic Potential. Handb. Exp Pharmacol. 181, 343-373, 2008;Y. Chernajovsky, A.Nissim (eds.) Therapeutic Antibodies, Springer-Verlag Berlin Heidelberg 2008.*
Katayama et al. A possible role for the loss of CD27-CD70 interaction in myelomagenesis. Br J Haematol. 120, 223-234, 2003.*
Wendtner et al. The Potential of Gene Transfer into Primary B-CLLCells Using Recombinant Virus Vectors. Leukemia & Lymphoma, 45, 897-904, 2008.*
Lobato et al., Intracellular antibodies and challenges facing their use as therapeutic agents. Trends Mol. Med. 9, 390-396, 2003.*
Christman, J.W. et al, "Nuclear Factor kappa B: A Pivotal Role in the Systemic Inflammatory Response Syndrome and New Target for Therapy", Intensive Care Med., 24:1131-1138 (1998).
Lin, X. et al., Molecular Determinants of NF-kappaB-Inducing Kinase Action, Molecular and Cellular Biology, 18(10):5899-5907 (1998).
Xiao, G. et al., "NF-kappaB-Inducing Kinase Regulates the Processing of NF-kappaB2 p100", Molecular Cell, 7:104-409 (2001).
Yin, L. et al., "Defective Lymphotoxin-beta Receptor-Induced NF-kappaB Transcriptional Activity in NIK-Deficient Mice", Science, 291:2162-2165 (2001).
Kumar et al., "Mechanical stress activates the nuclear factor-kappaB pathway in skeletal muscle fibers : A possible role in duchenne muscular dystrophy", 2003, Faseb J, 17:386-396.
PCT International Preliminary Report on Patentability, Jun. 7, 2006, in PCT/IL2004/001095.
Bodmer et al., The molecular architecture of the TNF superfamily, TRENDS in Biochemical Sciences, 27(1):19-26 (2002).

* cited by examiner

*Primary Examiner* — Elly-Gerald Stoica
(74) *Attorney, Agent, or Firm* — Browdy and Neimark, PLLC

(57) ABSTRACT

Methods and agents for immune modulation and methods for identifying putative immune modulators are provided.

3 Claims, 12 Drawing Sheets

1A

| Bait | Prey | Strength of interaction |
|---|---|---|
| NIK | SIVA-c | + |
| NIK | TRAF2 | - |
| NIK-(624-947) | SIVA-c | ++ |
| NIK-(624-947) | TRAF2 | + |
| SIVA-c | NIK-(624-947) | ++ |

1B

| myc-NIK | + | + | + | - | - | - |
|---|---|---|---|---|---|---|
| HIS-SIVA1 | - | + | - | - | + | - |
| HIS-SIVA2 | - | - | + | - | - | + |
| myc-*aly* NIK | - | - | - | + | + | + |

IP: anti-HIS  IP

WB: anti-myc  Total Lysate

1C

| HIS-SIVA1 | + | + | + | - | - | - |
|---|---|---|---|---|---|---|
| HIS-SIVA2 | - | - | - | + | + | + |
| myc-NIK | - | + | - | - | + | - |
| myc-*aly* NIK | - | - | + | - | - | + |

IP: anti-myc  IP

WB: anti-HIS  Total lysate

1D

1E

2D

2E

2F

2G

2H

3E

3F

3G

3H

4A

4C

4D

SEQUENCE LISTING

<160> NUMBER OF SEQ ID NOS: 15

<210> SEQ ID NO 1
<211> LENGTH: 2844
<212> TYPE: DNA
<213> ORGANISM: Homo sapiens

<400> SEQUENCE: 1

| | | | | | |
|---|---|---|---|---|---|
| atggcagtga | tggaaatggc | ctgcccaggt | gcccctggct | cagcagtggg | gcagcagaag | 60 |
| gaactcccca | agccaaagga | gaagacgccg | ccactgggga | agaaacagag | ctccgtctac | 120 |
| aagcttgagg | ccgtggagaa | gagccctgtg | ttctgcggaa | agtgggagat | cctgaatgac | 180 |
| gtgattacca | agggcacagc | caaggaaggc | tccgaggcag | ggccagctgc | catctctatc | 240 |
| atcgcccagg | ctgagtgtga | aatagccaa | gagttcagcc | ccacctttc | agaacgcatt | 300 |
| ttcatcgctg | gtccaaaaca | gtacagccag | tccgagagtc | ttgatcagat | ccccaacaat | 360 |
| gtggcccatg | ctacagaggg | caaaatggcc | cgtgtgtgtt | ggaagggaaa | gcgtcgcagc | 420 |
| aaagcccgga | gaaacggaa | gaagaagagc | tcaaagtccc | tggctcatgc | aggagtggcc | 480 |
| ttggccaaac | ccctccccag | gaccctgag | caggagagct | gcaccatccc | agtgcaggag | 540 |
| gatgagtctc | cactcggcgc | cccatatgtt | agaaacaccc | cgcagttcac | caagcctctg | 600 |
| aaggaaccag | gccttgggca | actctgtttt | aagcagcttg | gcgagggcct | acggccggct | 660 |
| ctgcctcgat | cagaactcca | caaactgatc | agcccttgc | aatgtctgaa | ccacgtgtgg | 720 |
| aaactgcacc | accccagga | cggaggcccc | ctgcccctgc | ccacgcaccc | cttcccctat | 780 |
| agcagactgc | ctcatccctt | cccattccac | cctctccagc | cctggaaacc | tcaccctctg | 840 |
| gagtccttcc | tgggcaaact | ggcctgtgta | gacagccaga | aacccttgcc | tgacccacac | 900 |
| ctgagcaaac | tggcctgtgt | agacagtcca | aagcccctgc | ctggcccaca | cctggagccc | 960 |
| agctgcctgt | ctcgtggtgc | ccatgagaag | ttttctgtgg | aggaatacct | agtgcatgct | 1020 |
| ctgcaaggca | gcgtgagctc | aagccaggcc | cacagcctga | ccagcctggc | caagacctgg | 1080 |
| gcagcacggg | gctccagatc | ccgggagccc | agccccaaaa | ctgaggacaa | cgagggtgtc | 1140 |
| ctgctcactg | agaaactcaa | gccagtggat | tatgagtacc | gagaagaagt | ccactgggcc | 1200 |
| acgcaccagc | tccgcctggg | cagaggctcc | ttcggagagg | tgcacaggat | ggaggacaag | 1260 |
| cagactggct | tccagtgcgc | tgtcaaaaag | gtgcggctgg | aagtatttcg | ggcagaggag | 1320 |
| ctgatggcat | gtgcaggatt | gacctcaccc | agaattgtcc | ctttgtatgg | agctgtgaga | 1380 |
| gaagggcctt | gggtcaacat | cttcatggag | ctgctggaag | gtggctccct | gggccagctg | 1440 |
| gtcaaggagc | agggctgtct | cccagaggac | cgggccctgt | actacctggg | ccaggccctg | 1500 |
| gagggtctgg | aatacctcca | ctcacgaagg | attctgcatg | gggacgtcaa | agctgacaac | 1560 |
| gtgctcctgt | ccagcgatgg | gagccacgca | gccctctgtg | actttggcca | tgctgtgtgt | 1620 |
| cttcaacctg | atggcctggg | aaagtccttg | ctcacagggg | actacatccc | tggcacagag | 1680 |
| acccacatgg | ctccggaggt | ggtgctgggc | aggagctgcg | acgccaaggt | ggatgtctgg | 1740 |
| agcagctgct | gtatgatgct | gcacatgctc | aacggctgcc | accctggac | tcagttcttc | 1800 |
| cgagggcgct | tctgcctcaa | gattgccagc | gagcctccgc | ctgtgaggga | gatcccaccc | 1860 |
| tcctgcgccc | ctctcacagc | ccaggccatc | caagaggggc | tgaggaaaga | gcccatccac | 1920 |
| cgcgtgtctg | cagcggagct | gggagggaag | gtgaaccggg | cactacagca | agtgggaggt | 1980 |
| ctgaagagcc | cttggagggg | agaatataaa | gaaccaagac | atccaccgcc | aaatcaagcc | 2040 |

-continued

```
aattaccacc agaccctcca tgcccagccg agagagcttt cgccaagggc cccagggccc    2100
cggccagctg aggagacaac aggcagagcc cctaagctcc agcctcctct cccaccagag    2160
cccccagagc caaacaagtc tcctcccttg actttgagca aggaggagtc tgggatgtgg    2220
gaacccttac ctctgtcctc cctggagcca gcccctgcca gaaacccccag ctcaccagag   2280 cggaaagcaa ccgtcccgga gcaggaactg cagcagctgg aaatagaatt attcctcaac    2340
agcctgtccc agccattttc tctggaggag caggagcaaa ttctctcgtg cctcagcatc    2400
gacagcctct ccctgtcgga tgacagtgag aagaacccat caaaggcctc tcaaagctcg    2460
cgggacaccc tgagctcagg cgtacactcc tggagcagcc aggccgaggc tcgaagctcc    2520
agctggaaca tggtgctggc ccgggggcgg cccaccgaca ccccaagcta tttcaatggt    2580
gtgaaagtcc aaatacagtc tcttaatggt gaacacctgc acatccggga gttccaccgg    2640
gtcaaagtgg gagacatcgc cactggcatc agcagccaga tcccagctgc agccttcagc    2700
ttggtcacca agacgggca gcctgttcgc tacgacatgg aggtgccaga ctcgggcatc     2760
gacctgcagt gcacactggc ccctgatggc agcttcgcct ggagctggag ggtcaagcat    2820
ggccagctgg agaacaggcc ctaa                                           2844

<210> SEQ ID NO 2
<211> LENGTH: 947
<212> TYPE: PRT
<213> ORGANISM: Homo sapiens

<400> SEQUENCE: 2

Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
    50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
    210                 215                 220

Glu Leu His Lys Leu Ile Ser Pro Leu Gln Cys Leu Asn His Val Trp
225                 230                 235                 240
```

```
Lys Leu His His Pro Gln Asp Gly Gly Pro Leu Pro Leu Pro Thr His
                245                 250                 255
Pro Phe Pro Tyr Ser Arg Leu Pro His Pro Phe Pro Phe His Pro Leu
            260                 265                 270
Gln Pro Trp Lys Pro His Pro Leu Glu Ser Phe Leu Gly Lys Leu Ala
        275                 280                 285
Cys Val Asp Ser Gln Lys Pro Leu Pro Asp Pro His Leu Ser Lys Leu
    290                 295                 300
Ala Cys Val Asp Ser Pro Lys Pro Leu Pro Gly Pro His Leu Glu Pro
305                 310                 315                 320
Ser Cys Leu Ser Arg Gly Ala His Glu Lys Phe Ser Val Glu Glu Tyr
                325                 330                 335
Leu Val His Ala Leu Gln Gly Ser Val Ser Ser Gln Ala His Ser
            340                 345                 350
Leu Thr Ser Leu Ala Lys Thr Trp Ala Ala Arg Gly Ser Arg Ser Arg
    355                 360                 365
Glu Pro Ser Pro Lys Thr Glu Asp Asn Glu Gly Val Leu Leu Thr Glu
370                 375                 380
Lys Leu Lys Pro Val Asp Tyr Glu Tyr Arg Glu Val His Trp Ala
385                 390                 395                 400
Thr His Gln Leu Arg Leu Gly Arg Gly Ser Phe Gly Glu Val His Arg
                405                 410                 415
Met Glu Asp Lys Gln Thr Gly Phe Gln Cys Ala Val Lys Lys Val Arg
            420                 425                 430
Leu Glu Val Phe Arg Ala Glu Leu Met Ala Cys Ala Gly Leu Thr
        435                 440                 445
Ser Pro Arg Ile Val Pro Leu Tyr Gly Ala Val Arg Glu Gly Pro Trp
    450                 455                 460
Val Asn Ile Phe Met Glu Leu Leu Glu Gly Gly Ser Leu Gly Gln Leu
465                 470                 475                 480
Val Lys Glu Gln Gly Cys Leu Pro Glu Asp Arg Ala Leu Tyr Tyr Leu
                485                 490                 495
Gly Gln Ala Leu Glu Gly Leu Glu Tyr Leu His Ser Arg Arg Ile Leu
            500                 505                 510
His Gly Asp Val Lys Ala Asp Asn Val Leu Leu Ser Ser Asp Gly Ser
        515                 520                 525
His Ala Ala Leu Cys Asp Phe Gly His Ala Val Cys Leu Gln Pro Asp
    530                 535                 540
Gly Leu Gly Lys Ser Leu Leu Thr Gly Asp Tyr Ile Pro Gly Thr Glu
545                 550                 555                 560
Thr His Met Ala Pro Glu Val Val Leu Gly Arg Ser Cys Asp Ala Lys
                565                 570                 575
Val Asp Val Trp Ser Ser Cys Cys Met Met Leu His Met Leu Asn Gly
            580                 585                 590
Cys His Pro Trp Thr Gln Phe Phe Arg Gly Pro Leu Cys Leu Lys Ile
        595                 600                 605
Ala Ser Glu Pro Pro Val Arg Glu Ile Pro Pro Ser Cys Ala Pro
    610                 615                 620
Leu Thr Ala Gln Ala Ile Gln Glu Gly Leu Arg Lys Glu Pro Ile His
625                 630                 635                 640
Arg Val Ser Ala Ala Glu Leu Gly Gly Lys Val Asn Arg Ala Leu Gln
                645                 650                 655
Gln Val Gly Gly Leu Lys Ser Pro Trp Arg Gly Glu Tyr Lys Glu Pro
```

```
                        660                 665                 670
Arg His Pro Pro Pro Asn Gln Ala Asn Tyr His Gln Thr Leu His Ala
            675                 680                 685
Gln Pro Arg Glu Leu Ser Pro Arg Ala Pro Gly Pro Arg Pro Ala Glu
        690                 695                 700
Glu Thr Thr Gly Arg Ala Pro Lys Leu Gln Pro Pro Leu Pro Pro Glu
705                 710                 715                 720
Pro Pro Glu Pro Asn Lys Ser Pro Pro Leu Thr Leu Ser Lys Glu Glu
                725                 730                 735
Ser Gly Met Trp Glu Pro Leu Pro Leu Ser Ser Leu Glu Pro Ala Pro
            740                 745                 750
Ala Arg Asn Pro Ser Ser Pro Glu Arg Lys Ala Thr Val Pro Glu Gln
            755                 760                 765
Glu Leu Gln Gln Leu Glu Ile Glu Leu Phe Leu Asn Ser Leu Ser Gln
        770                 775                 780
Pro Phe Ser Leu Glu Glu Gln Glu Gln Ile Leu Ser Cys Leu Ser Ile
785                 790                 795                 800
Asp Ser Leu Ser Leu Ser Asp Asp Ser Glu Lys Asn Pro Ser Lys Ala
                805                 810                 815
Ser Gln Ser Ser Arg Asp Thr Leu Ser Ser Gly Val His Ser Trp Ser
            820                 825                 830
Ser Gln Ala Glu Ala Arg Ser Ser Trp Asn Met Val Leu Ala Arg
            835                 840                 845
Gly Arg Pro Thr Asp Thr Pro Ser Tyr Phe Asn Gly Val Lys Val Gln
        850                 855                 860
Ile Gln Ser Leu Asn Gly Glu His Leu His Ile Arg Glu Phe His Arg
865                 870                 875                 880
Val Lys Val Gly Asp Ile Ala Thr Gly Ile Ser Ser Gln Ile Pro Ala
                885                 890                 895
Ala Ala Phe Ser Leu Val Thr Lys Asp Gly Gln Pro Val Arg Tyr Asp
            900                 905                 910
Met Glu Val Pro Asp Ser Gly Ile Asp Leu Gln Cys Thr Leu Ala Pro
            915                 920                 925
Asp Gly Ser Phe Ala Trp Ser Trp Arg Val Lys His Gly Gln Leu Glu
        930                 935                 940
Asn Arg Pro
945

<210> SEQ ID NO 3
<211> LENGTH: 175
<212> TYPE: PRT
<213> ORGANISM: Homo sapiens

<400> SEQUENCE: 3

Met Pro Lys Arg Ser Cys Pro Phe Ala Asp Val Ala Pro Leu Gln Leu
1               5                   10                  15
Lys Val Arg Val Ser Gln Arg Glu Leu Ser Arg Gly Val Cys Ala Glu
            20                  25                  30
Arg Tyr Ser Gln Glu Val Phe Glu Lys Thr Lys Arg Leu Leu Phe Leu
        35                  40                  45
Gly Ala Gln Ala Tyr Leu Asp His Val Trp Asp Glu Gly Cys Ala Val
    50                  55                  60
Val His Leu Pro Glu Ser Pro Lys Pro Gly Pro Thr Gly Ala Pro Arg
65                  70                  75                  80
Ala Ala Arg Gly Gln Met Leu Ile Gly Pro Asp Gly Arg Leu Ile Arg
```

```
                    85                  90                  95
Ser Leu Gly Gln Ala Ser Glu Ala Asp Pro Ser Gly Val Ala Ser Ile
            100                 105                 110

Ala Cys Ser Ser Cys Val Arg Ala Val Asp Gly Lys Ala Val Cys Gly
            115                 120                 125

Gln Cys Glu Arg Ala Leu Cys Gly Gln Cys Val Arg Thr Cys Trp Gly
            130                 135                 140

Cys Gly Ser Val Ala Cys Thr Leu Cys Gly Leu Val Asp Cys Ser Asp
145                 150                 155                 160

Met Tyr Glu Lys Val Leu Cys Thr Ser Cys Ala Met Phe Glu Thr
                165                 170                 175

<210> SEQ ID NO 4
<211> LENGTH: 110
<212> TYPE: PRT
<213> ORGANISM: Homo sapiens

<400> SEQUENCE: 4

Met Pro Lys Arg Ser Cys Pro Phe Ala Asp Val Ala Pro Leu Gln Leu
1               5                   10                  15

Lys Val Arg Val Ser Gln Arg Glu Leu Ser Arg Gly Val Cys Ala Glu
            20                  25                  30

Arg Tyr Ser Gln Glu Val Phe Asp Pro Ser Gly Val Ala Ser Ile Ala
        35                  40                  45

Cys Ser Ser Cys Val Arg Ala Val Asp Gly Lys Ala Val Cys Gly Gln
    50                  55                  60

Cys Glu Arg Ala Leu Cys Gly Gln Cys Val Arg Thr Cys Trp Gly Cys
65                  70                  75                  80

Gly Ser Val Ala Cys Thr Leu Cys Gly Leu Val Asp Cys Ser Asp Met
                85                  90                  95

Tyr Glu Lys Val Leu Cys Thr Ser Cys Ala Met Phe Glu Thr
            100                 105                 110

<210> SEQ ID NO 5
<211> LENGTH: 10
<212> TYPE: PRT
<213> ORGANISM: Artificial sequence
<220> FEATURE:
<223> OTHER INFORMATION: Myc tag

<400> SEQUENCE: 5

Glu Gln Lys Leu Ile Ser Glu Glu Asp Leu
1               5                   10

<210> SEQ ID NO 6
<211> LENGTH: 528
<212> TYPE: DNA
<213> ORGANISM: Homo sapiens

<400> SEQUENCE: 6
atgcccaagc ggagctgccc cttcgcggac gtggccccgc tacagctcaa ggtccgcgtg    60
agccagaggg agttgagccg cggcgtgtgc gccgagcgct actcgcagga ggtcttcgag   120
aagaccaagc gactcctgtt cctcggggcc caggcctacc tggaccacgt gtgggatgaa   180
ggctgtgccg tcgttcacct gccagagtcc ccaaagcctg ccctacaggg gccccgagg   240 gctgcacgtg gcagatgctg attggaccag acggccgcct gatcaggag ccttgggcag   300 gcctccgaag ctgaccccat ctggggtagcg tccattgcct gttcctcatg cgtgcgagcc   360
gtggatggga aggcggtctg cggtcagtgt gagcgagccc tgtgcgggca gtgtgtgcgc   420
```

```
acctgctggg gctgcggctc cgtggcctgt accctgtgtg gcctcgtgga ctgcagtgac    480
atgtacgaga aagtgctgtg caccagctgt gccatgttcg agacctga                528
```

\<210\> SEQ ID NO 7
\<211\> LENGTH: 333
\<212\> TYPE: DNA
\<213\> ORGANISM: Homo sapiens

\<400\> SEQUENCE: 7

```
atgcccaagc ggagctgccc cttcgcggac gtggccccgc tacagctcaa ggtccgcgtg     60
agccagaggg agttgagccg cggcgtgtgc gccgagcgct actcgcagga ggtcttcgac    120
ccatctgggg tagcgtccat tgcctgttcc tcatgcgtgc gagccgtgga tgggaaggcg    180
gtctgcggtc agtgtgagcg agccctgtgc gggcagtgtg tgcgcacctg ctggggctgc    240
ggctccgtgg cctgtaccct gtgtggcctc gtggactgca gtgacatgta cgagaaagtg    300
ctgtgcacca gctgtgccat gttcgagacc tga                                 333
```

\<210\> SEQ ID NO 8
\<211\> LENGTH: 34
\<212\> TYPE: DNA
\<213\> ORGANISM: Artificial sequence
\<220\> FEATURE:
\<223\> OTHER INFORMATION: Single strand DNA oligonucleotide

\<400\> SEQUENCE: 8

```
ccaagctatt tcaatcgtgt gaaagtccaa atac                                 34
```

\<210\> SEQ ID NO 9
\<211\> LENGTH: 34
\<212\> TYPE: DNA
\<213\> ORGANISM: Artificial sequence
\<220\> FEATURE:
\<223\> OTHER INFORMATION: Single strand DNA oligonucleotide

\<400\> SEQUENCE: 9

```
gtatttggac tttcacacga ttgaaatagc ttgg                                 34
```

\<210\> SEQ ID NO 10
\<211\> LENGTH: 16
\<212\> TYPE: PRT
\<213\> ORGANISM: Artificial sequence
\<220\> FEATURE:
\<223\> OTHER INFORMATION: A peptide corresponding to a sequence within
      the NIK kinase domain

\<400\> SEQUENCE: 10

```
Arg Leu Gly Arg Gly Ser Phe Gly Glu Val His Arg Met Glu Asp Lys
1               5                   10                  15
```

\<210\> SEQ ID NO 11
\<211\> LENGTH: 42
\<212\> TYPE: DNA
\<213\> ORGANISM: Artificial sequence
\<220\> FEATURE:
\<223\> OTHER INFORMATION: Single strand DNA oligonucleotide

\<400\> SEQUENCE: 11

```
gagggtctgg aatacctaca ttcccgcagg attctgcatg gg                        42
```

\<210\> SEQ ID NO 12
\<211\> LENGTH: 42
\<212\> TYPE: DNA
\<213\> ORGANISM: Artificial sequence

```
<220> FEATURE:
<223> OTHER INFORMATION: Single strand DNA oligonucleotide

<400> SEQUENCE: 12
cccatgcaga atcctgcggg aatgtaggta ttccagaccc tc                    42

<210> SEQ ID NO 13
<211> LENGTH: 64
<212> TYPE: DNA
<213> ORGANISM: Artificial sequence
<220> FEATURE:
<223> OTHER INFORMATION: Single strand DNA oligonucleotide

<400> SEQUENCE: 13
gatcccctac ctccactcac gaaggattca agagatcctt cgtgagtgga ggtattttg   60 gaaa                                                              64

<210> SEQ ID NO 14
<211> LENGTH: 64
<212> TYPE: DNA
<213> ORGANISM: Artificial sequence
<220> FEATURE:
<223> OTHER INFORMATION: Single strand DNA oligonucleotide

<400> SEQUENCE: 14
agcttttcca aaatacctc cactcacgaa ggatctcttg aatccttcgt gagtggaggt   60
aggg                                                              64

<210> SEQ ID NO 15
<211> LENGTH: 19
<212> TYPE: DNA
<213> ORGANISM: Artificial sequence
<220> FEATURE:
<223> OTHER INFORMATION: NIK SiRNA sequence corresponding with
      nucleotides 1513 1531

<400> SEQUENCE: 15
tacctccact cacgaagga                                              19
```

METHOD FOR TREATING AN IMMUNE DISORDER BY DECREASING NIK-SIVA COMPLEX FORMATION

FIELD OF THE INVENTION

The present invention relates to methods of regulating an immune response in an individual and, more particularly, to methods and agents which target NIK and NIK binding proteins participating in both the canonical and alternative NF-κB activation pathway, to methods of identifying molecules/agents for modulation of NIK activity and to the molecules/agents obtainable by the method thereof.

BACKGROUND OF THE INVENTION

The NF-κB/Rel family of transcription factors is active in inflammatory and immune cell response, cell cycle regulation, differentiation and protection from apoptosis [Baeuerle and Baltimore, Cell 87:13-20, (1996); Ghosh, et al., Annu. Rev. Immunol. 16:225-260, (1998)]. In mammals, this family of transcription factors is comprised of five members: p65 (RelA), RelB, c-Rel, NF-κB1 (which occurs both as a precursor, p105, and in a processed form, p50) and NF-κB2 (which occurs both as a precursor, p100, and as its processed product, p52). The NF-κB protein homo- and heterodimers exist in the cytoplasm, in complex with inhibitors of the IκB family. The precursor forms of NF-κB1 and NF-κB2 (p105 and p100, respectively) contain C-terminal IκB-homologous inhibitory regions. Dimers containing these NF-κB proteins are retained in the cytoplasm by virtue of the function of the IκB-homologous regions. Moreover NF-κB1/p105 and NF-κB2/p100 can also associate with dimers of other NF-κB proteins and impose cytoplasmic retention on them. NF-κB activation occurs mainly through induced degradation of the IκB proteins or of IκB homologous regions in NF-κB1/p105 and NF-κB2/p100, and consequent translocation of the NF-κB dimers to the nucleus. The induced degradation of the IκB proteins provides the most important mechanism regulating NF-κB activity (Baeuerle and Baltimore, 1996) (Ghosh et al., 1998) (Ghosh and Karin, 2002).

Most of the knowledge of these processes concerns the mechanisms of activation of a ubiquitous NF-κB dimer, p65:p50. The critical event initiating this 'canonical' pathway is activation of an IκB-phosphorylating protein kinase, IKK2. IKK2 occurs within a macromolecular complex, the 'IKK signalosome', in association with a structurally homologous kinase, IKK1, and an adapter protein, NEMO. IKK2-mediated phosphorylation of IκB leads to its proteasomal degradation and hence activation of its associated NF-κB dimers (Karin and Ben-Neriah, 2000).

Other studies have yielded some knowledge of an 'alternative' pathway through which NF-κB dimers containing NF-κB2/p100 are activated. This activation occurs independently of IKK2 or NEMO, but is dependent on IKK1. Phosphorylation of p100 upon activation of this pathway leads to limited proteolytic processing in which only the IκB-homologous region within p100 is degraded. This process allows the resulting p52 fragment to translocate to the nucleus in association with some other NF-κB proteins (mainly RelB) (Xiao et al., 2001) (Senftleben et al., 2001) (Solan et al., 2002) (Coope et al., 2002) (Claudio et al., 2002) (Kayagaki et al., 2002) (Dejardin et al., 2002) (Yilmaz et al., 2003) (Hatada et al., 2003).

The proteins of the tumor necrosis factor/nerve growth factor (TNF/NGF) receptor family are a group of cell-surface receptors critically involved in the maintenance of homeostasis of the immune system. These proteins interact with their corresponding ligands, either to induce cell death or promote cell survival of immune cells. The biologic function of this group of proteins has been closely associated with the regulation of the immune response and the pathogenesis of autoimmune disease. [Zhou et al., Immunol. Res. 26:323-336, (2002)]. The TNF receptors control multiple immune-defense activities as well as certain developmental processes through NF-κB activation (Wallach et al., 1999) (Locksley et al., 2001). Most of these receptors are capable of activating the canonical NF-κB pathway. In addition, the lymphotoxin-β receptor (LTβR), whose expression is restricted to stromal cells and several receptors that occur in lymphocytes (CD40, BLyS/BAFF and as shown in the present work—CD27), also activate the alternative pathway (Dejardin et al., 2002) (Coope et al., 2002) (Claudio et al., 2002) (Kayagaki et al., 2002) (Hatada et al., 2003).

Signaling for NF-κB activation by several receptors of the TNF receptor family is initiated by their binding to adapter proteins of the TRAF family. In cells treated with TNF the TRAFs have been shown to facilitate, collaboratively with the adapter protein RIP, recruitment of the signalosome components to the p55 TNF receptor (Zhang et al., 2000) (Devin et al., 2000) (Devin et al., 2001). Additional protein that participates in NF-κB activation by the TNF/NGF receptor family was identified as a 'NF-κB-inducing kinase' (NIK), (Malinin et al., 1997).

Initially NIK was suggested to mediate activation of the canonical NF-κB pathway in response to multiple inducers with many different physiological functions (Malinin et al., 1997). However, later studies of mice of the aly strain, which express a non-functional NIK mutant, as well as of NIK-knockout mice, challenged the notion that NIK has a functional role in the activities of most of these inducers. They suggested rather, that NIK participates selectively in the activation of NF-κB by a restricted set of ligands that specifically affect the development and function of lymphocytes (Shinkura et al., 1999) (Yin et al., 2001). Moreover, based on characterization of cells derived from these mutant mice, it was suggested that NIK does not participate at all in the canonical NF-κB pathway, but rather serves exclusively to activate the alternative one (Pomerantz and Baltimore, 2002). Lymphocytes of NIK-mutant mice exhibit a highly aberrant pattern of differentiation (Miyawaki et al., 1994) (Shinkura et al., 1999) (Matsumoto et al., 1999) (Yamada et al., 2000) (Karrer et al., 2000) (Fagarasan et al., 2000), therefore, the present work aimed to re-assess the signaling role of NIK in lymphocytes.

In the present, the function of NIK in lymphocytes was now re-evaluated by assessing the effect of its depletion or inhibition in vitro in cultured cells of lymphoblastoid lines. The assays showing that NIK is not required for activation of the canonical pathway by TNF in lymphocytes were confirmed. However, as detailed below, NIK was found to play a crucial role in these cells in activation of the alternative as well as of the canonical pathway by CD40 ligand (CD40L) and BLyS/BAFF induction. Furthermore, CD27 (Camerini et al., 1991), a receptor of the TNF/NGF family that is expressed mainly in T lymphocytes and memory B lymphocytes and was previously suggested to activate NF-κB (Yamamoto et al., 1998) in a NIK-independent manner (Akiba et al., 1998) was shown to initiate the alternative pathway. I was also found by the inventors that NIK binds to SIVA, a protein associated with CD27 (Prasad et al., 1997), and mediates both the canonical and the alternative NF-κB-activating pathways in response to this receptor. Although NIK was not required for activation of the signalosome by the p55 TNF receptor, activation of the signalosome by CD27 did depend on NIK. Moreover, unlike triggering by the p55 TNF receptor, triggering by CD27 induced, in a NIK-dependent way, selective recruitment of IKK1 to this receptor, a process that might be the initiating event in the NIK-dependent activation of both NF-κB pathways by CD27.

The biologic function of members of the NIK-dependent NF-κB pathway has been closely associated with the regulation of the immune response and the pathogenesis of autoimmune disease.

It is shown in accordance with the present invention that NIK, in contrast to prior art teachings, does participate in the canonical NF-κB activating pathway. In addition, it is shown that NIK participates in an alternative NF-κB pathway which is induced by BlyS and CD40L and have identified CD70 as a novel inducer of this alternative pathway.

As such, the present findings establish the role of NIK in NF-κB activation and thus provide the motivation to utilize various NIK targeting agents in treatment of various immune diseases.

SUMMARY OF THE INVENTION

The invention relates to the use of an agent capable of increasing or decreasing NIK-SIVA complex formation, in the manufacture of a medicament for the treatment of an immune disorder. More specifically, the said immune disorder is characterized by abnormal function or level of at least one protein selected from the group consisting of BlyS/BAFF, CD27, SIVA and NIK. Example of immune disorders according to the invention are multiple myeloma (MM), acquired immunodeficiency syndrome (AIDs), Sjogren's syndrome (SS), B-cells chronic lymphocytic leukemia (B-CLL), systemic lupus erythematosus, inflammatory colon disease, systemic inflammatory response syndrome (SIRS), multiple organ disinfection syndrome (MODS) and acute respiratory distress syndrome (ARDS).

In one aspect, the invention provides the use of an agent capable of increasing or decreasing NIK-dependent CD27 regulation in the manufacture of a medicament for treating an immune disorder. Particularly, the invention provides the use of an agent such as antibody capable of binding NIK, e.g. an antibody directed against the phosphorylated NIK activation loop, or a small interfering RNA molecule, e.g. that set forth in SEQ ID NO: 15, or a rybozyme, for decreasing NIK-dependent CD27 regulation.

In another aspect, the invention provides the use of an agent capable of decreasing or increasing the activity of NIK in the manufacture of a medicament for treating an immune disorder caused or aggravated by the abnormal NF-κB activation via the canonical pathway. Particularly, the invention provides the use of an agent such as antibody capable of binding NIK, e.g. an antibody directed against the phosphorylated NIK activation loop, or a small interfering RNA molecule, e.g. that set forth in SEQ ID NO: 15, or a rybozyme, for decreasing NIK-dependent CD27 regulation.

More specifically, said abnormal NF-κB activation may be caused by induction of CD40L, Blys, CD70 and/or activation of the receptor thereof.

In addition, the invention provides a method of treating an immune disorder comprising administering to an individual having the immune disorder a therapeutically effective amount of an agent capable of increasing or decreasing NIK-SIVA complex formation, thereby treating the immune disorder in the individual. Particularly, said immune disorder is characterized by abnormal function or level of at least one protein selected from the group consisting of BlyS/BAFF, CD27, SIVA and NIK. More specifically, the method according the invention can be use to treat multiple myeloma (MM), acquired immunodeficiency syndrome (AIDs), Sjogren's syndrome (SS), B-cells chronic lymphocytic leukemia (B-CLL), systemic lupus erythematosus, inflammatory colon disease, systemic inflammatory response syndrome (SIRS), multiple organ disinfection syndrome (MODS) and acute respiratory distress syndrome (ARDS). In one embodiment of the invention, the administration of the agent modulating NIK-SIVA interaction can be effected by expressing said agent within cells, such as lymphocytes, of said individual.

Also, the invention relates to a method of treating an immune disorder comprising administering to an individual having the immune disorder a therapeutically effective amount of an agent capable of increasing or decreasing NIK-dependent CD27 regulation, thereby treating the immune disorder in the individual.

In particular, the administration may be effected by expressing said agent within cells such as lymphocytes of said individual.

In a further embodiment, the invention relates to a method of treating an immune disorder caused or aggravated by abnormal NF-κB activation by the canonical pathway, comprising administering to an individual suffering from the disorder a therapeutically effective amount of an agent capable of decreasing or increasing the activity of NIK. Particularly, the abnormal NF-κB activation may be caused by induction of CD40L, CD70, or Blys and/or activation of the receptor thereof.

In one particular embodiment of the invention, the method involves the use of an agent capable of decreasing the activity of NIK, for example an antibody directed against the phosphorylated NIK activation loop, a small interfering RNA molecule such as the one of SEQ ID NO: 15, or a rybozyme.

The invention provides also, an isolated polynucleotide comprising a nucleic acid sequence capable of specifically down-regulating NIK expression in cells provided thereto such a an small interfering RNA molecule like the one of SEQ ID NO:15, a construct comprising such polynucleotide and a cell comprising the nucleic acid construct.

In another embodiment, the invention provides an antibody or antibody fragment capable of specifically binding to an amino acid sequence region set forth by coordinates 624-947 of SEQ ID NO:2, 123-175 of SEQ ID NO:3 and/or 58-110 of SEQ ID NO:4

In addition, the invention provides a method of identifying a putative immune modulator, the method comprising identifying a molecule capable of increasing or decreasing NIK-SIVA complex formation, said molecule being the putative immune modulator.

Also the invention provides a method of identifying a putative immune modulator, the method comprising identifying a molecule capable of increasing or decreasing NIK-dependent CD27 regulation, said molecule being the putative immune modulator.

Moreover the invention provides a method for the screening (or identification and/or selection) of molecules capable of modulating the activity of NIK comprising contacting a cell with a ligand of a TNF/NGF receptor family capable to induce NIK-dependent canonical and alternative pathway in the cell, incubating the cell prior to, after, or during said contacting with individual tested molecules, detecting activation of the canonical pathway in the cell and selecting individual molecule/s capable of modulating induction of the canonical pathway induced by said ligand.

In one aspect, the invention provides a method for the screening (identification and/or selection) of molecules capable of modulating NIK activity comprising contacting a lymphoblastoid cell with a ligand of a TNF/NGF receptor family capable of activating NIK and the canonical pathway in the cell, incubating the cell prior to, after, or during said contacting, with individual tested molecules, detecting activation of the canonical pathway and, selecting individual molecule/s capable of modulating induction of the canonical pathway induced by said ligand but not by any other ligand capable of inducing canonical pathway in a NIK independent manner.

In one embodiment of the invention, the ligand used for the screening method is selected from CD70, CD40L, or Blys/BAFF.

In another embodiment of the invention, the cells for the screening method are of a lymphoblastoid type such as for e.g. Ramos, Raji or BJAB cells.

In a further embodiment of the invention, activation of the canonical pathway is detected in the screening method by monitoring parameters indicative of the canonical pathway activation, such as IκB degradation, IκBα phosphorylation and p65 translocation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a illustrates yeast two-hybrid binding assays of NIK to SIVA. The binding of NIK and its C-terminally mutant (NIK 624-947) to the C-terminal part of SIVA (amino acids 123-175 in SIVA1 or 58-110 in SIVA2) or TRAF2, was assessed using transformed SFY526 yeast. The development of a strong color reaction within 1 hour and 3 hours is indicted as '++' and '+', respectively; '−' indicates no color development within 24 h. This assay shows that the C-terminal SIVA fragment binds to the C-terminal part of NIK and this binding is stronger than that observed with the full-length NIK protein.

Figure 1:
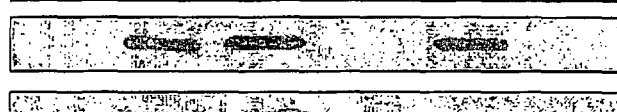
FIGS. 1a-e illustrate binding of NIK to SIVA.
Figure 1:
Figure 1:
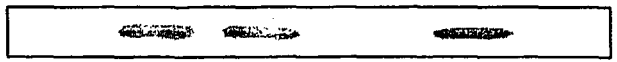
Figure 1:
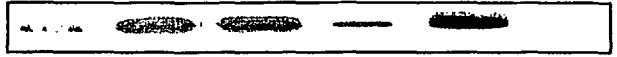
Figure 1:
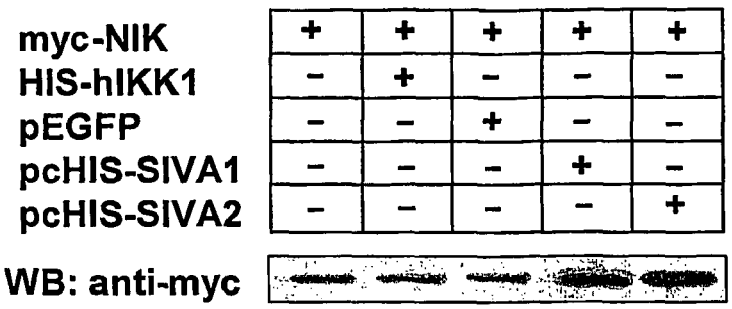
Figure 1:
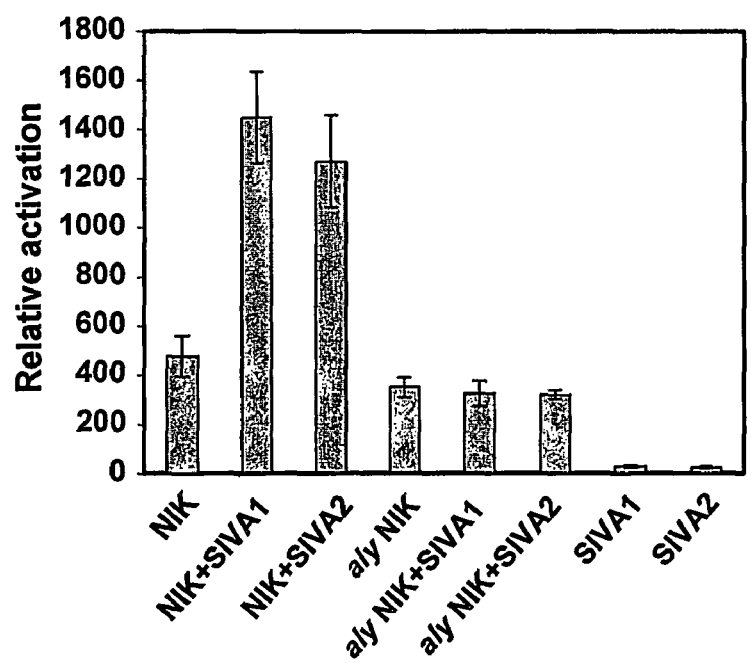

The top panel of FIG. 1b is a table representing the transfection pattern of HEK293T cells with plasmids expressing myc-NIK, HIS-SIVA1, HIS-SIVA2 or myc-aly NIK. '+' indicates that the corresponding plasmid was used for transfection, otherwise '−' is indicated.

The middle panel of FIG. 1b represents a co-immunoprecipitation of NIK (or of NIK into which a missense mutation corresponding to that found in aly mice was introduced) with SIVA using antibodies against the HIS fused to SIVA1 and SIVA2. Co-immunoprecipitation was assessed after 24 h.

The bottom panel of FIG. 1b is a western blot analysis on total cell lysate with antibodies against myc tag fused to NIK and aly MK.

The top panel of FIG. 1c is a table representing the transfection pattern of HEK293T cells with plasmids expressing HIS-SIVA1, HIS-SIVA2 myc-NIK, or myc-aly NIK. '+' indicates that the corresponding plasmid was used for transfection, otherwise '−' is indicated.

The middle panel of FIG. 1c is a co-immunoprecipitation of SIVA with NIK from transiently transfected HEK293T cells using antibodies against the myc fused to NIK and aly NIK, co-immunoprecipitation was assessed after 24 h. The bottom panel of FIG. 1c is a western blot analysis on total cell lysate with antibodies against HIS tag fused to SIVA1 and SIVA2. FIGS. 1b and 1c show that NIK co-immunoprecipitate bidirectionally with SIVA1 and SIVA2 and 'aly NIK' co-immunoprecipitate with SIVA1 and to a small extent also with SIVA2.

The top panel of FIG. 1d is a table representing the transfection pattern of HEK293T cells with plasmids expressing myc-NIK, HIS-hIKK1, pEGFP, pcHIS-SIVA1 or pcHIS-SIVA2. '+' indicates that the corresponding plasmid was used for transfection, otherwise '−' is indicated.

The bottom panel of FIG. 1d is a western blot analysis on total cell lysate using antibodies against the myc tag fused to NIK. This figure demonstrates that the quantity of NIK in the transfected cells is increased by the co-expression with SIVA1 or SIVA2. FIG. 1e is a bar graph illustrating the enhancement of NIK-mediated NF-κB activation by co-expressed SIVA. The effect of over-expression of NIK or aly NIK, alone or together with SIVA1 or SIVA2, on HIV-luciferase expression in HEK293T cells was assessed 24 hours after transfection. Values are the means obtained in two experiments in which each test was carried out in triplicate. The graph shows that SIVA is capable of affecting NIK function.

FIGS. 2a-h illustrate the induction of both the canonical and the alternative pathways in lymphocytes by CD70 (CD27 ligand) and the effect of NIK deficiency on this induction.

Figure 2:
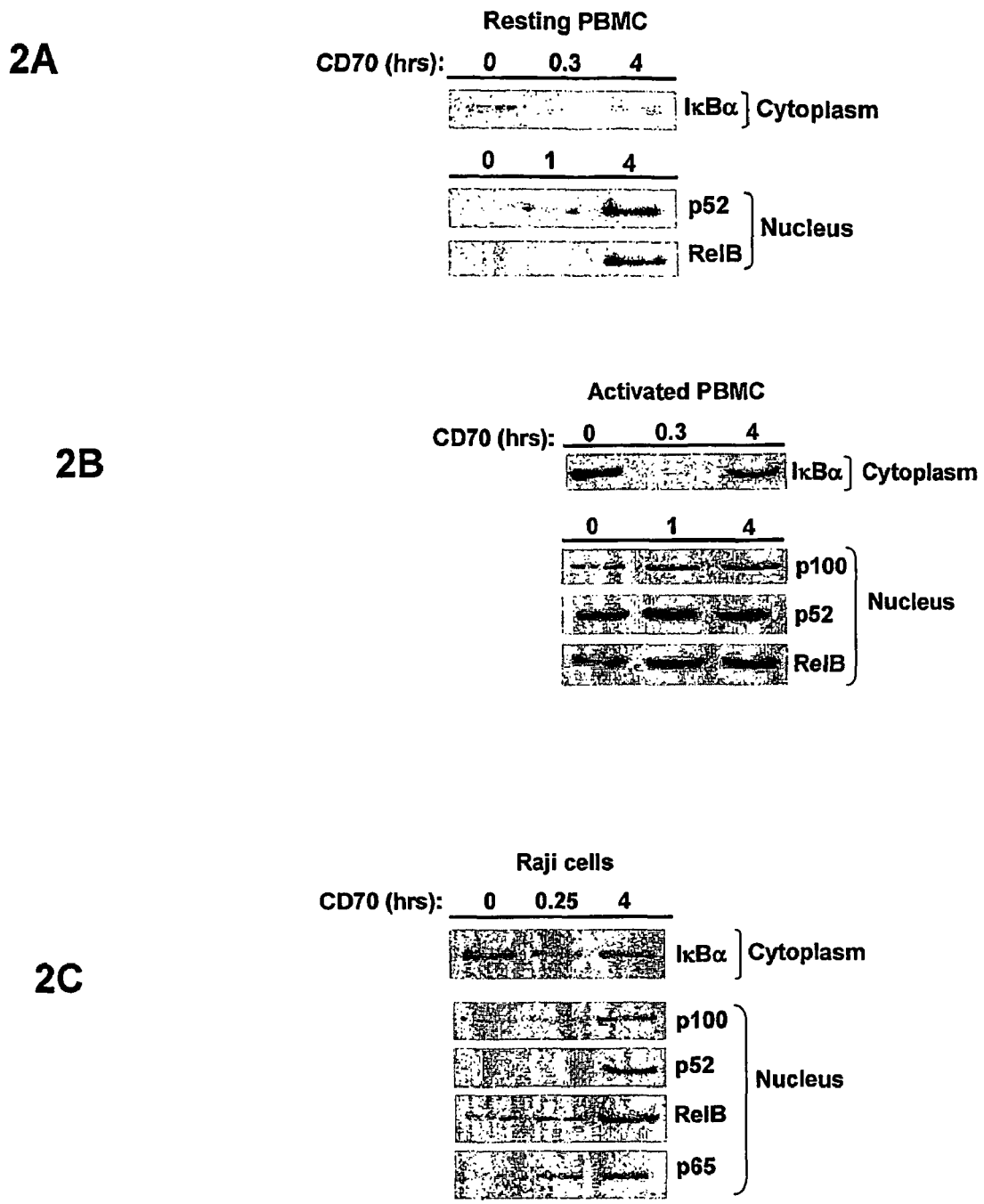
Figure 2:
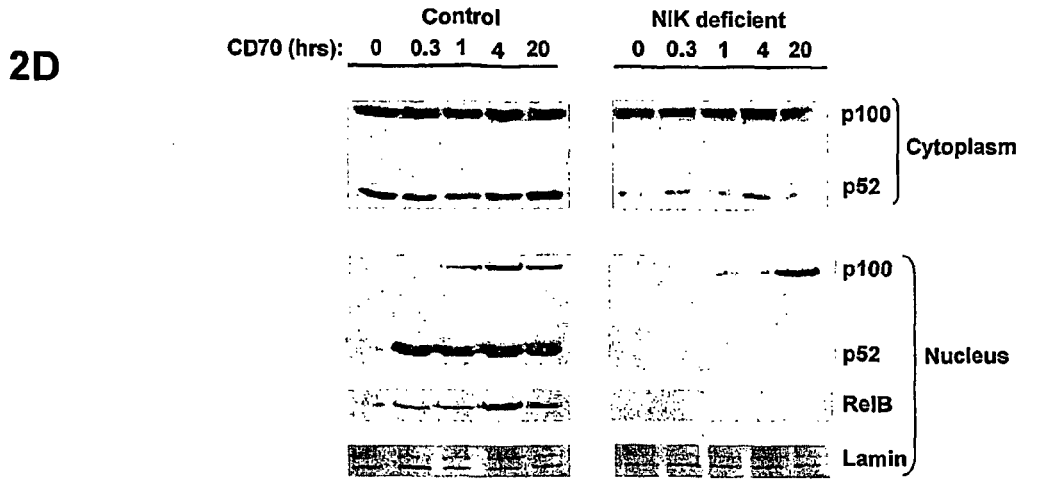
Figure 2:
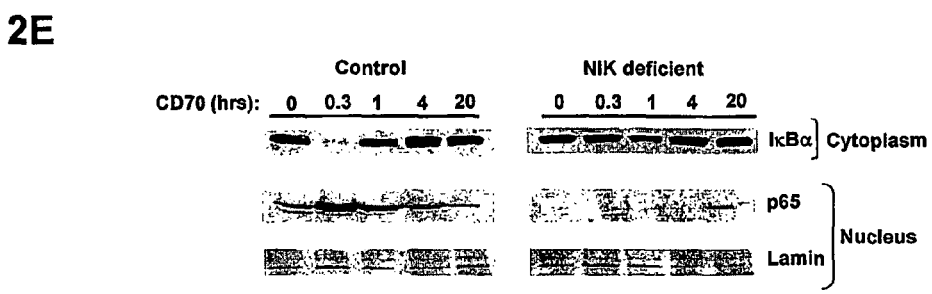
Figure 2:
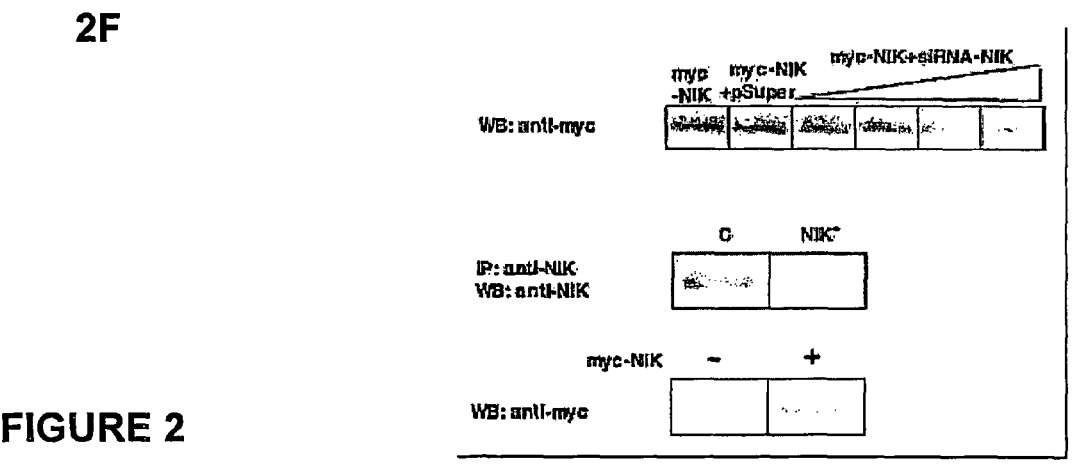
Figure 2:
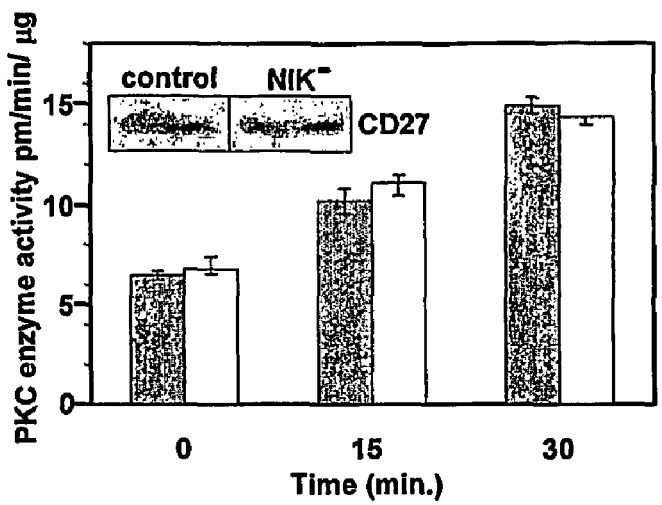
Figure 2:
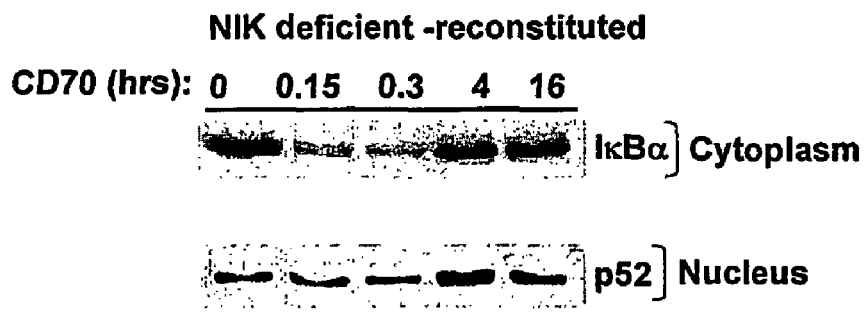

FIG. 2a is a western blot analysis designed for detecting IκBα levels in the cytoplasm of resting PBMC following CD70 application and p52 and RelB levels in the nucleus of resting PBMC following CD70 treatment. This figure demonstrates rapid decrease of IκBα as well as translocation of NF-κB2/p52 (p52) and RelB to the nuclei.

FIG. 2b is a western blot analysis designed for detecting IκBα levels in the cytoplasm of stimulated PBMC and p100, p52 and RelB levels in the nucleus of stimulated PBMC upon CD70 treatment. This figure shows rapid decrease of IκBα.

FIG. 2c is a western blot analysis designed for detecting IκBα levels in the cytoplasm of Raji cells and p100, p52, RelB and p65 levels in the nucleus of Raji cells upon CD70 treatment. This figure shows that IκBα degradation as well as nuclear translocation of RelB and NF-κB2/p52.

FIG. 2d is a western blot analysis designed for detecting p100 and p52 levels in the cytoplasm of normal and NIK$^{(MINUS)}$ Ramos cells and p100, p52 and RelB levels in the nucleus of these cells upon CD70 treatment. This figure demonstrates the induction of nuclear translocation of RelB and NF-κB2/p52 in normal Ramos cells, as well as delayed p100 nuclear translocation in NIK$^{(MINUS)}$ Ramos cells. FIG. 2e is a western blot analysis designed for detecting IκBα levels in the cytoplasm of normal and NIK$^{(MINUS)}$ Ramos cells and p65 levels in the nucleus of these cells upon CD70 treatment. This figure demonstrates IκBα degradation as well as nuclear translocation of p65 in normal Ramos cells.

FIG. 2f demonstrates the suppression of NIK synthesis by expression of NIK siRNA.

The top panel of FIG. 2f depicts a western blot analysis designed for detecting NIK levels in HEK293 cells transiently expressing myc-tagged NIK and co-transfected with pSUPER-NIK at ratios of 1:1, 1:2, 1:3 and 1:5. This figure shows that NIK is effectively suppressed.

The middle panel of FIG. 2f depicts a western blot analysis designed for detecting NIK levels in Ramos cells constitutively expressing lentiviral-pSUPER-NIK (NIK$^{(MINUS)}$ cells) in comparison to Ramos cells transduced with lentiviral-GFP as control. This figure shows that NIK is effectively suppressed.

The bottom panel of FIG. 2f depicts a western blot analysis designed for detecting NIK levels in NIK$^{(MINUS)}$ Ramos cells to which NIK expression was reinstated by constitutively expressing myc-tagged NIK. This figure demonstrates that NIK expression was reinstated.

FIG. 2g is a bar graph demonstrating CD70-induced protein kinase C (PKC) activation in normal (black bars) and NIK$^{(MINUS)}$ (white bars) Ramos cells. PKC activation was performed in cell lysate using the Signatect PKC assay system at various time points (0, 15 and 30 minutes) following CD70 application to the cells. Bars represent the means of triplicate tests. CD27 levels in normal and NIK$^{(MINUS)}$ Ramos cells are shown in the inset. This figure shows that NIK$^{(MINUS)}$ Ramos cells express CD27 at levels comparable to those in normal Ramos cells and manifest a normal extent of protein kinase C (PKC) activation upon CD27 triggering.

FIG. 2h is a western blot analysis designed for detecting IκBα levels in the cytoplasm of NIK$^{(MINUS)}$ reconstituted Ramos cells and p52 levels in the nucleus of these cells. This figure demonstrates these cells regain the ability to respond to CD70 with both an increase in nuclear p52 and a transient decrease in IκBα.

FIGS. 3a-i demonstrate the induction of both the canonical and the alternative NF-κB pathways by CD40L, BLyS/BAFF, TNF, thapsigargin or PMA and the effect of NIK deficiency on this induction.

Figure 3:
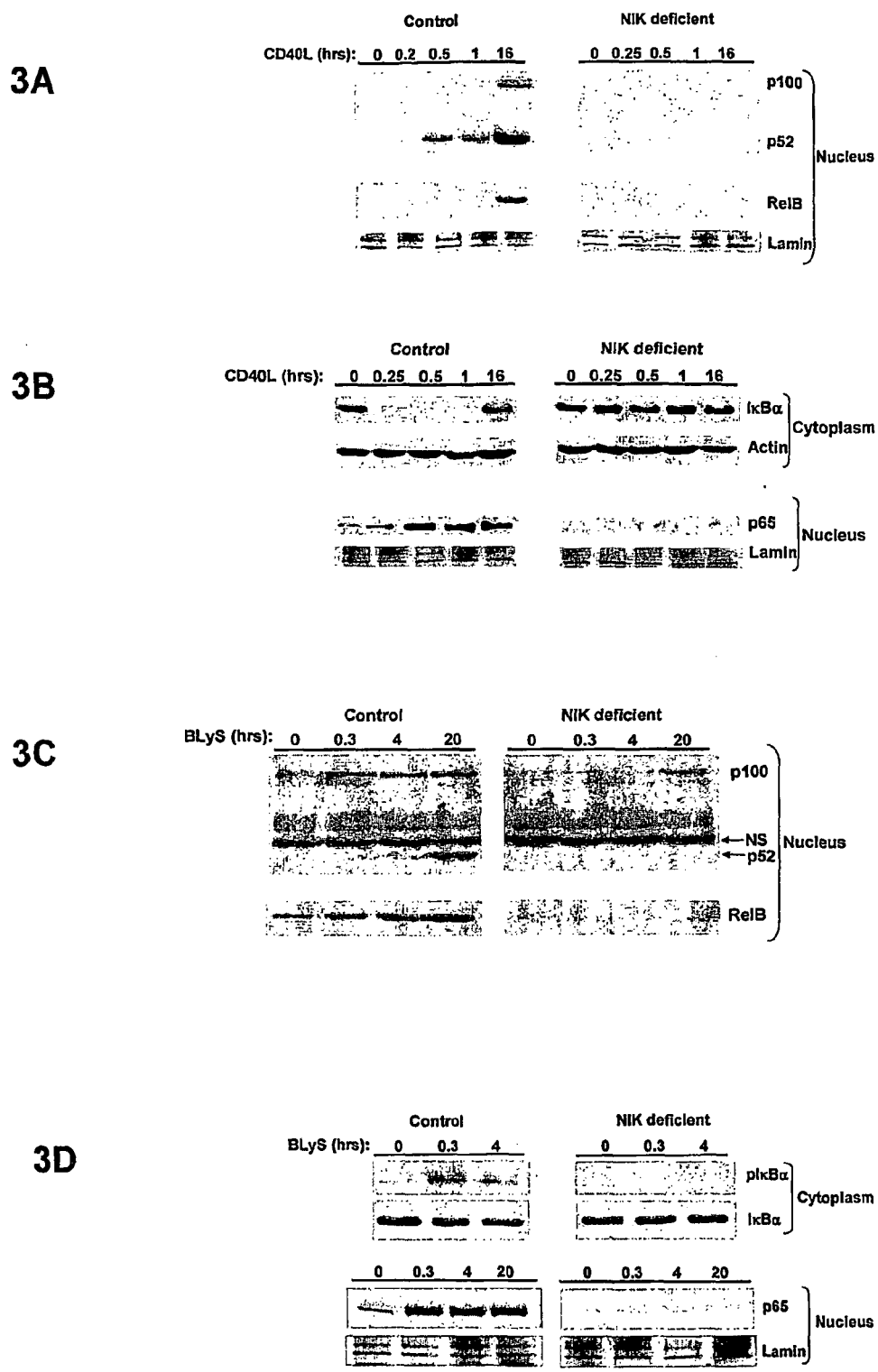
Figure 3:
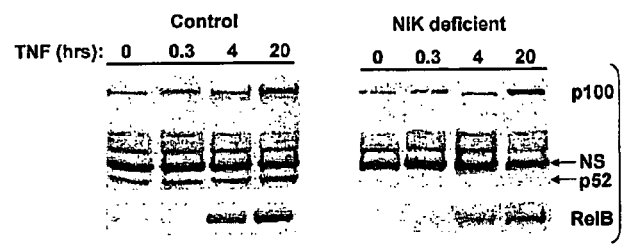
Figure 3:
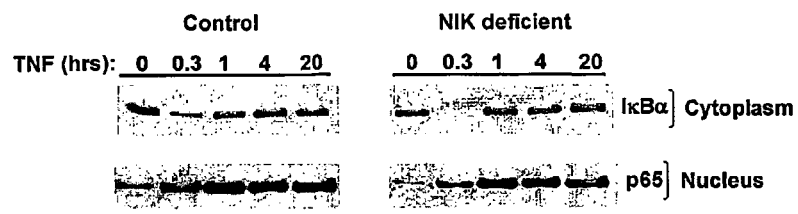
Figure 3:
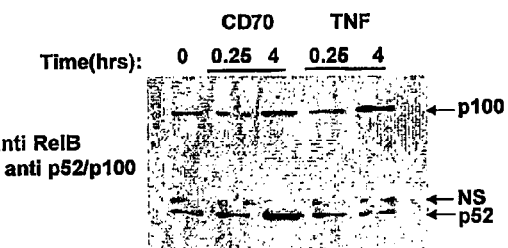
Figure 3:
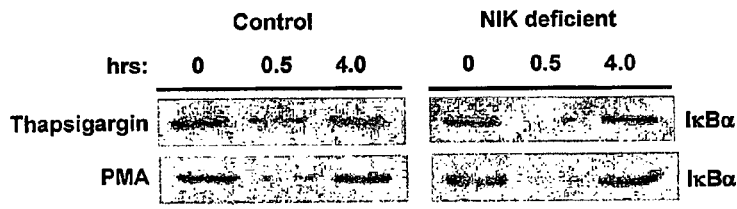

FIG. 3a is a western blot analysis designed for detecting p100, p52 and RelB levels in the nucleus of normal and NIK$^{(MINUS)}$ Ramos cells following CD40L treatment. This figure demonstrates induction of nuclear translocation of p100, p52 and RelB in normal Ramos cells.

FIG. 3b is a western blot analysis designed for detecting IκBα levels in the cytoplasm of normal and NIK$^{(MINUS)}$ Ramos cells and p65 levels in the nucleus of these cells following CD40L treatment. This figure demonstrates rapid induction of nuclear translocation of p65 associated with a decrease in IκBα in normal Ramos cells.

FIG. 3c is a western blot analysis designed for detecting p100, p52 and RelB levels in the nucleus of normal and NIK$^{(MINUS)}$ Ramos cells following BLyS treatment. This figure demonstrates the induction of nuclear translocation of p52 and RelB in normal Ramos cells.

FIG. 3d is a western blot analysis designed for detecting phosphorylated IκBα levels in the cytoplasm of normal and NIK$^{(MINUS)}$ Ramos cells and p65 levels in the nucleus of these cells following BLyS treatment. The figure demonstrates rapid nuclear translocation of p65 associated with phosphorylation of IκBα with no visible change in its cellular levels in normal Ramos cells.

FIG. 3e is a western blot analysis designed for detecting p100, NS, p52 and RelB levels in the nucleus of normal and NIK$^{(MINUS)}$ Ramos cells following TNF treatment. This figure demonstrates induction of nuclear translocation of p100 and RelB but only a slight increase in nuclear p52 in normal Ramos cells and a nuclear translocation of p100 and RelB in NIK$^{(MINUS)}$ Ramos cells.

FIG. 3f is a western blot analysis designed for detecting IκBα levels in the cytoplasm of normal and NIK$^{(MINUS)}$ Ramos cells and p65 levels in the nucleus of these cells following TNF treatment. The figure shows the induction of IκBα degradation and nuclear translocation of p65 in both, normal and NIK$^{(MINUS)}$ Ramos.

FIG. 3g is an immunoprecipitation analysis with RelB of various NF-κB proteins from nuclear extracts of the Ramos cells, 15 minutes and 4 hours after the application of TNF or CD70 to the cells. Levels of p100, NS and p52 were detected by western blot analysis. This figure demonstrates that CD70 enhances nuclear accumulation of RelB:p52 and RelB:p100 while TNF induces increased nuclear levels of only RelB:p100.

FIG. 3h is a western blot analysis designed for detecting IκBα levels in the cytoplasm of normal and NIK$^{(MINUS)}$ Ramos cells in response to thapsigargin or 4β-phorbol-12-myristate-13-acetate (PMA). This figure demonstrates that NIK depletion has no effect on IκBα degradation.

FIG. 3i is a western blot analysis showing that p65, whose expression is independent of NF-κB, occurs in NIK$^{(MINUS)}$ cells in normal amounts.

FIGS. 4a-d demonstrate that the induction of IκBα degradation by CD40L and BLyS and not by TNF is blocked by α-pNIK antibodies against the phosphorylated activation loop.

Figure 4:
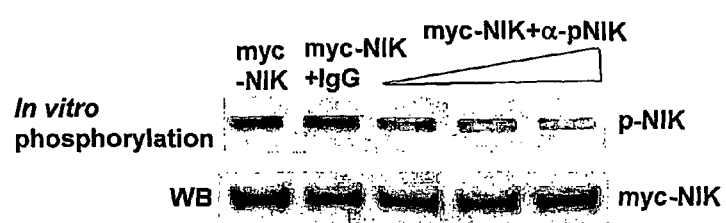
Figure 4:
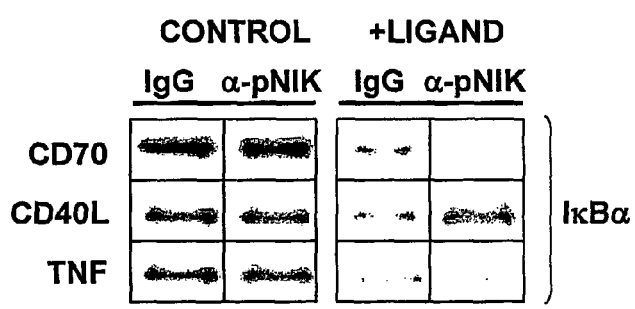
Figure 4:
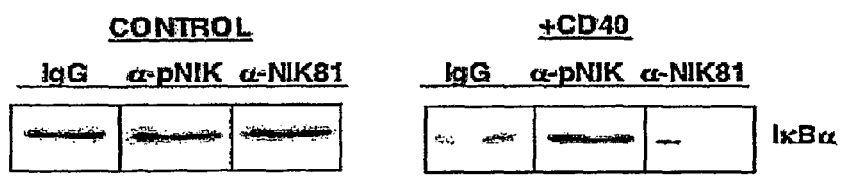
Figure 4B:
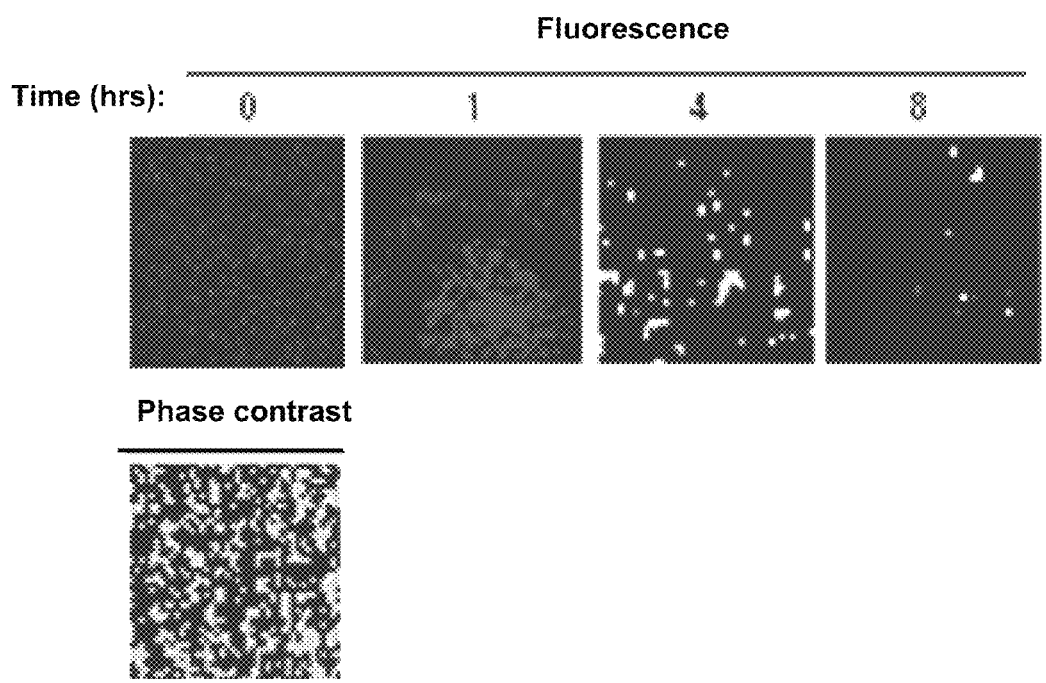

FIG. 4a is an autoradiogram of the phosphorylated protein as compared with a western blot analysis of NIK levels in the same samples. Self-phosphorylation of myc-NIK immunoprecipitated from transiently transfected HEK293T cells in the presence of 0 μg, 0.5 μg, 1.0 μg and 2 μg of α-pNIK antibodies or with control 2 μg IgG. This figure demonstrates that α-pNIK effectively blocks the in-vitro kinase function of NIK. FIG. 4b demonstrates introduction of antibodies into Ramos cells using a protein-transfection reagent.

FIG. 4b is a photograph of uptake of FITC-tagged immunoglobulin by Ramos cells, assessed by fluorescent microscopy at various times (0, 1, 4 and 8 hours) after transfection. This figure demonstrates that treatment of Ramos cells with a protein-transfection kit allows effective, though transient, introduction of immunoglobulins into the cells.

FIG. 4c is a western blot analysis designed for detecting degradation of IκBα induced by CD70, CD40L or TNF in Ramos cells with α-pNIK antibody. This figure demonstrates that α-pNIK antibody effectively blocks the induction of IκBα degradation by CD70 or CD40L.

FIG. 4d is a western blot analysis designed for detecting degradation of IκBα by CD40L in BJAB cells with α-pNIK antibody. This figure demonstrates that CD40L induces IκBα degradation in these cells and this induction is significantly reduced in the presence of α-pNIK antibodies.

FIGS. 5a-d demonstrate the effect of CD70 or TNF on recruitment of IKK's and activation of the IKK signalosome in normal and NIK$^{(MINUS)}$ Ramos cells.

Figure 5:
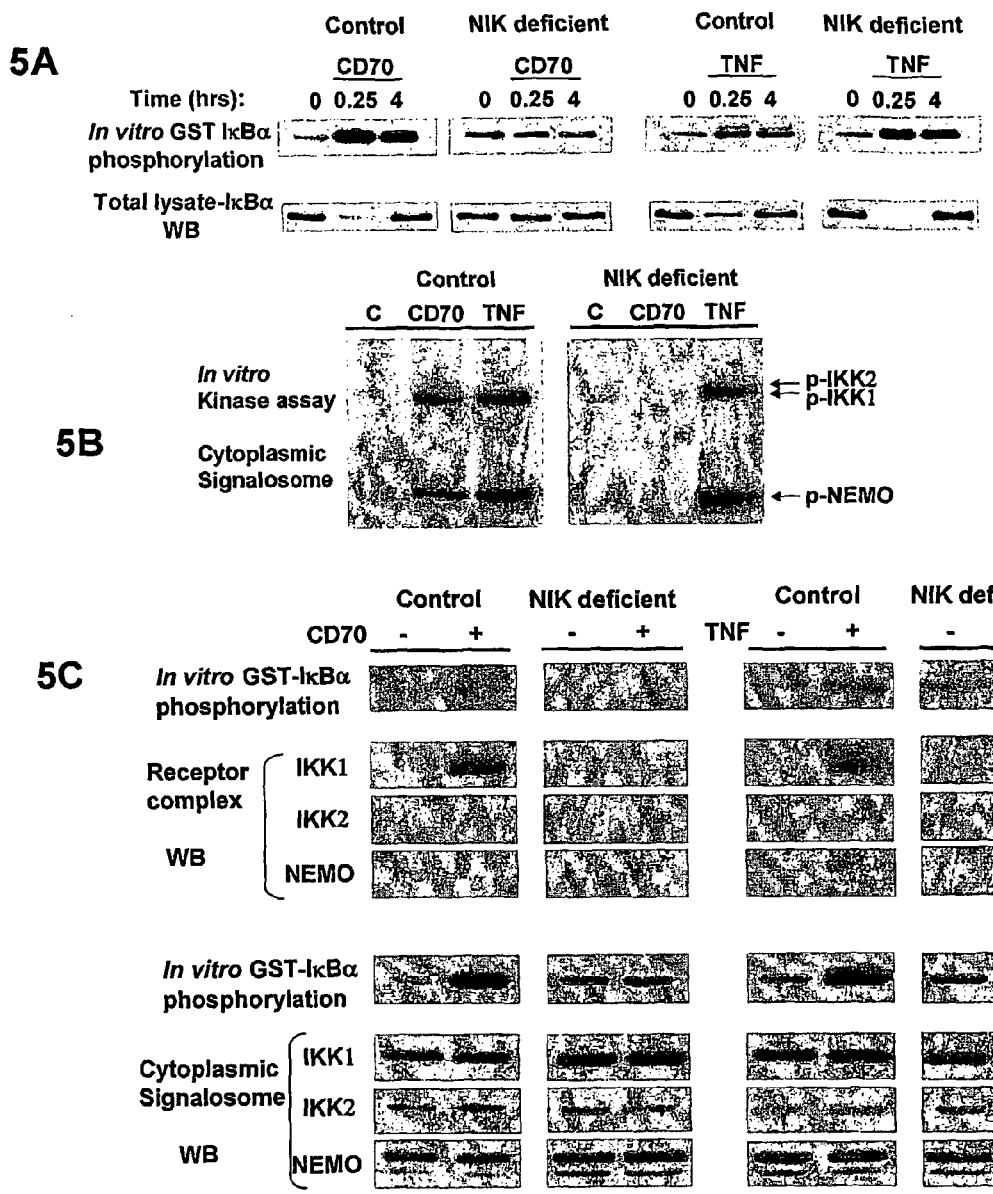
Figure 5:
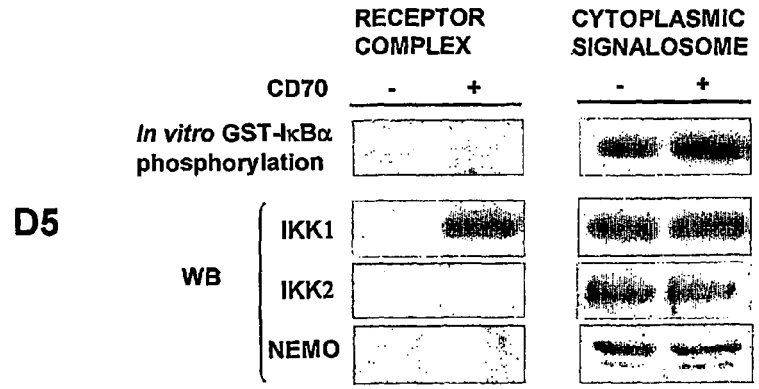

FIG. 5a (top panel) is a kinetic analysis of in-vitro IκBα phosphorylation activity of the IKK signalosome in Ramos cells, isolated by immunoprecipitation using antibodies to IKK1, as compared with western blot analysis (bottom panel) designed for detecting cellular IκBα levels, at indicated times (0, 15 minutes or 4 hours) after application of CD70 or TNF to normal and NIK$^{(MINUS)}$ Ramos cells. This figure demonstrates that both TNF and CD70 enhance the in vitro kinase function of the IKK signalosome in normal Ramos cells. In NIK deficient Ramos cells, CD70 induced activation of the signalosome was blocked and there was no in-vitro IκB phosphorylation, while TNF-induced activation of the signalosome was not affected at all.

FIG. 5b demonstrates self-phosphorylation of the IKKs and phosphorylation of NEMO in in-vitro kinase test of the IKK signalosome isolated 15 minutes after application of CD70 or TNF to normal and NIK$^{(MINUS)}$ Ramos cells. This figure demonstrates that both TNF and CD70 enhance self-phosphorylation of the IKKs and phosphorylation of NEMO in normal Ramos cells. The effect of CD70 on the signalosome is aborted in the NIK$^{(MINUS)}$ Ramos cells.

FIG. 5c demonstrates the recruitment of IKK1, IKK2 and NEMO by CD70 or TNF induction in normal and NIK$^{(MINUS)}$ Ramos cells. The top panel of FIG. 5c demonstrates in-vitro IκBα phosphorylation activity and presence of the IKK signalosome components in the receptor complexes associated with CD27 (left) and the p55 TNF receptor (right) isolated from normal and NIK$^{(MINUS)}$ Ramos cells before and after stimulation with CD70 or TNF for 15 min.

The bottom panel of FIG. 5c demonstrates in-vitro IκBα phosphorylation activity and western blot analysis designed for detecting the IKK signalosomes isolated from Ramos cells at the same times as the receptor complexes were isolated. The amounts of IKK1 introduced into the kinase tests corresponded to those shown in this figure. This figure demonstrates that TNF induces the recruitment of all three components of the signalosome (IKK1, IKK2, and NEMO), in about the same ratio as that found in the complex that they form in the cytosol both in normal and NIK$^{(MINUS)}$ Ramos cells. CD70 induces the recruitment of only IKK1 in normal Ramos cells.

FIG. 5d demonstrates an in-vitro IκBα phosphorylation activity and a western blot analysis designed for detecting the presence of IKK signalosome components in the receptor complexes associated with CD27 and signalosome preparations isolated from resting PBMC before and after stimulation with CD70 for 15 min. This figure demonstrates that CD70 induces the selective recruitment of IKK1.

FIGS. 6a-d demonstrate that CD70 induces recruitment of the IKK signalosome followed by selective recruitment of IKK1 to CD27 in a way that depends on NIK kinase function, as well as recruitment of NIK independently of its kinase function.

FIG. 6a shows a kinetic analysis of recruitment of TRAF2 and RIP, the components of the IKK signalosome (IKK1, IKK2, and NEMO), the components of the canonical NF-κB complex (IκBα, p65, and p50), and p100 to CD27 and p55 TNF receptor complexes in Ramos cells at various time points after CD70 or TNF application, compared to composition of the cytoplasmic IKK signalosome (isolated, prior to stimulation, by the use of antibody to NEMO; right), and to the cellular levels of IκBα (bottom).

FIGS. 6b, 6c show in-vitro IκB phosphorylation activity and the presence of IKK signalosome components in the receptor complexes and cytoplasmic signalosomes.

FIG. 6b shows CD27 complexes and signalosome preparations isolated from resting PBMC before stimulation, and after stimulation with CD27 for 20 min.

FIG. 6c shows the receptor complexes associated with CD27 (left) and p55 TNF receptor (right) isolated from control and NIK– Ramos cells before stimulation, and after stimulation with CD70 or TNF for 20 min.

FIG. 6d shows the comparison of the kinetics of recruitment of NIK and IKK1 to CD27 and to the p55 TNF receptor complexes at various times after application of CD70 or TNF to NIK– cells replenished with wild type or enzymatically inactive NIK mutant (KD-NIK).

Figure 7:
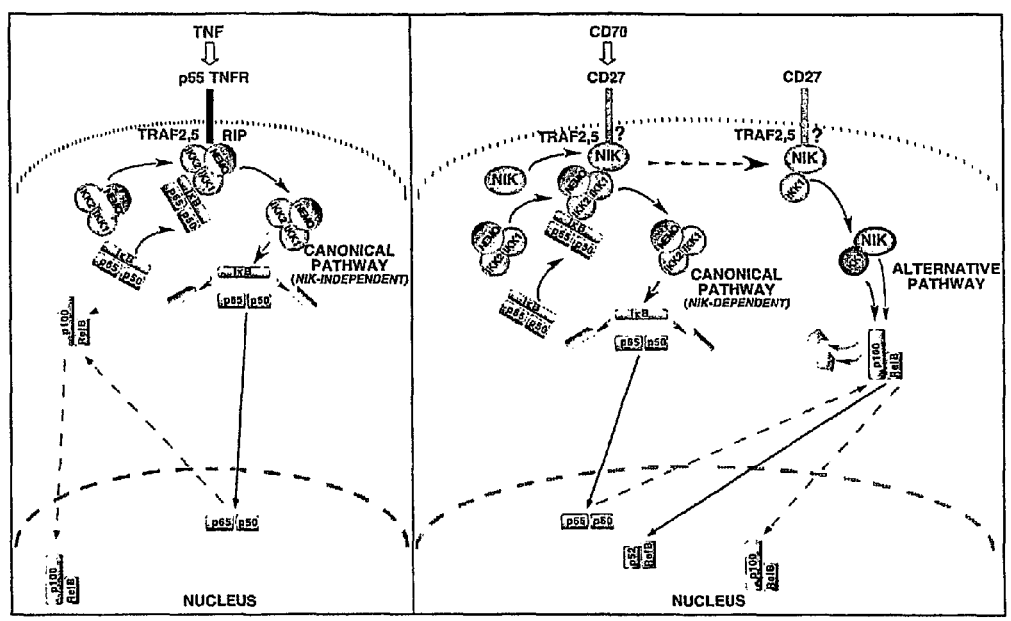

FIG. 7 depicts a speculative model of the mechanisms initiating NF-κB activation by TNF (left panel) and CD70 (right panel). The figure presents an outline of the molecular events leading from activation of the p55 TNF receptor by TNF (left) and of the CD27 receptor by CD70 (right) to NF-κB activation. TNF induces NIK-independent recruitment of all three core components of the signalosome to its receptor in a way that depends on interacrion of these components with TRAFs and RIP. This recruitment initiates the canonical pathway only. CD70 induces recruitment and massive ubiquitination of TRAF2, but not RIP. It also induces the recruitment of NIK and, in a way that depends on the kinase function of NIK, induces also the recruitment first of the whole signalosome and then of only IKK to CD27. Recruitment of whole signalosome to this receptor and the consequent activation of IKK1 in it by NIK might be the mechanism for initiation by this receptor of the canonical pathway, and the subsequent recruitment of IKK1 might be the mechanism for initiation by thus receptor of the alternative pathway. Broken lines represent the induction of p100 and RelB upon activation of the canonical pathway by TNF and CD70 and the consequent translocation of the p100:RelB complex to the nucleous.

DESCRIPTION OF THE PREFERRED EMBODIMENTS

The present invention relates to the use of agents capable of increasing or decreasing the activity of NIK in immune disorders caused or aggravated by abnormal NF-κB activation via the canonical pathway. In another aspect, the invention relates to the use of an agent capable of increasing or decreasing NIK-SIVA complex formation in the treatment of immune disorders.

The present invention relates also to methods for the screening (identification and/or selection) of molecules capable of modulating (increasing or decreasing) the activity of NIK, and to the molecules obtainable by the methods thereof.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The NF-κB family of transcription factors are associated with a large number of biological functions including inflammatory and immune cell response, cell cycle regulation, differentiation and protection from apoptosis [Baeuerle and Baltimore, Cell 87:13-20, (1996); Ghosh, et al., Annu. Rev. Immunol. 16:225-260, (1998)]. The majority of these activities have been realized from studies of NF-κB function in regulation of lymphocyte survival and activation.

It is well established that controlled activation of NF-κB is essential for normal innate and adaptive immune responses, and that abnormal regulation of NF-κB signaling in lymphocytes results in development of diseases ranging from chronic inflammation and autoimmunity to lymphoma [Ruland, and Mak, Semin. Immunol. 3:177-83, (2003)]. Accordingly, arrest of NF-κB signals by blocking ligand-receptor interactions enables effective suppression of signaling activities which are associated with T and B lymphocyte activation and growth, inflammation, fibroblast proliferation, and cell death. Therefore, regulation of NF-κB activities can be proven beneficial to treatment of various disorders, which are associated with the above described cell signaling activities.

NF-κB activation results from the activation of at least one of two parallel signaling pathways, termed canonical and alternative, described in details in the preceding Background section.

One of the key elements in NF-κB activation is the NF-κB inducing kinase (NIK). While this protein has been initially implicated in the activation of the canonical NF-κB pathway in response to multiple inducers [N. L. Malinin, M. P. Boldin, A. V. Kovalenko, D. Wallach, Nature 385, 540-4 (1997); H. Akiba et al., J Biol Chem 273, 13353-8. (1998)], these referenced prior art studies were based on the ability of overexpressed NIK mutants to block signaling, an approach which is now considered unreliable as is evident from the fact that the same experimental approach provided evidence that NIK functions in TNF activation of the canonical pathway, a finding that has since then been refuted [L. Yin et al., Science 291, 2162-5. (2001)].

Thus, more recent studies refute early findings and provide overwhelming evidence that NIK does not participate in activation of the canonical pathway and that studies that suggested that NIK participates in CD27 signaling were erroneous [S. Ghosh, M. Karin, Cell 109 Suppl, S81-96 (April 2002); E. Dejardin et al., Immunity 17, 525-35 (October 2002) and J. L. Pomerantz, D. Baltimore, Mol Cell 10, 693-5 (October 2002).

Thus, although NIK inhibition has been suggested as a possible therapeutic approach in treatment of systemic inflammatory response syndrome, it is highly unlikely that NIK inhibitory agents will be utilized as efficacious drugs, in diseases which are caused or aggravated by NF-κB activation trough the canonical pathway, since at present the scientific community clearly doubts the role of NIK in activating the canonical pathway.

In accordance with the present invention it has been established that NIK, in contrast to prior art teachings, does participate in the canonical NF-κB activating pathway. In addition, it has been found that NIK also participates in activation of the alternative NF-κB pathway via CD70/CD27 signaling.

The present findings establish a role for NIK in NF-κB activation and thus provide the motivation to utilize various NIK targeting agents in treatment of various immune diseases, which are caused or aggravated by NF-κB activation.

As is illustrated in the Examples section which follows, the present inventors have established that NIK plays a crucial role in activation of the alternative as well as of the canonical pathway by CD40 ligand (CD40L), BLyS/BAFF and CD27. Furthermore, NIK was found to bind SIVA, a protein associated with CD27 (Prasad et al., 1997), and to thereby mediate both the canonical and the alternative NF-κB-activating pathways in response to this receptor. Although NIK was not required for activation of the signalosome by the p55 TNF receptor, activation of the signalosome by CD27 did depend on NIK. Moreover, unlike triggering by the p55 TNF receptor, triggering by CD27 induced, in a NIK-dependent way, selective recruitment of IKK1 to this receptor, a process that might be the initiating event in the NIK-dependent activation of both NF-κB pathways by CD27.

Elucidation of the alternative and canonical NF-κB activating pathways which is enabled by the present study (see FIG. 6), allows for the design of refined therapies aimed to specifically blocking the deleterious effects of unregulated activity of the transducers and effectors of these pathways.

Thus, the present invention provides a method of treating an immune disorder in an individual.

Figure 6:
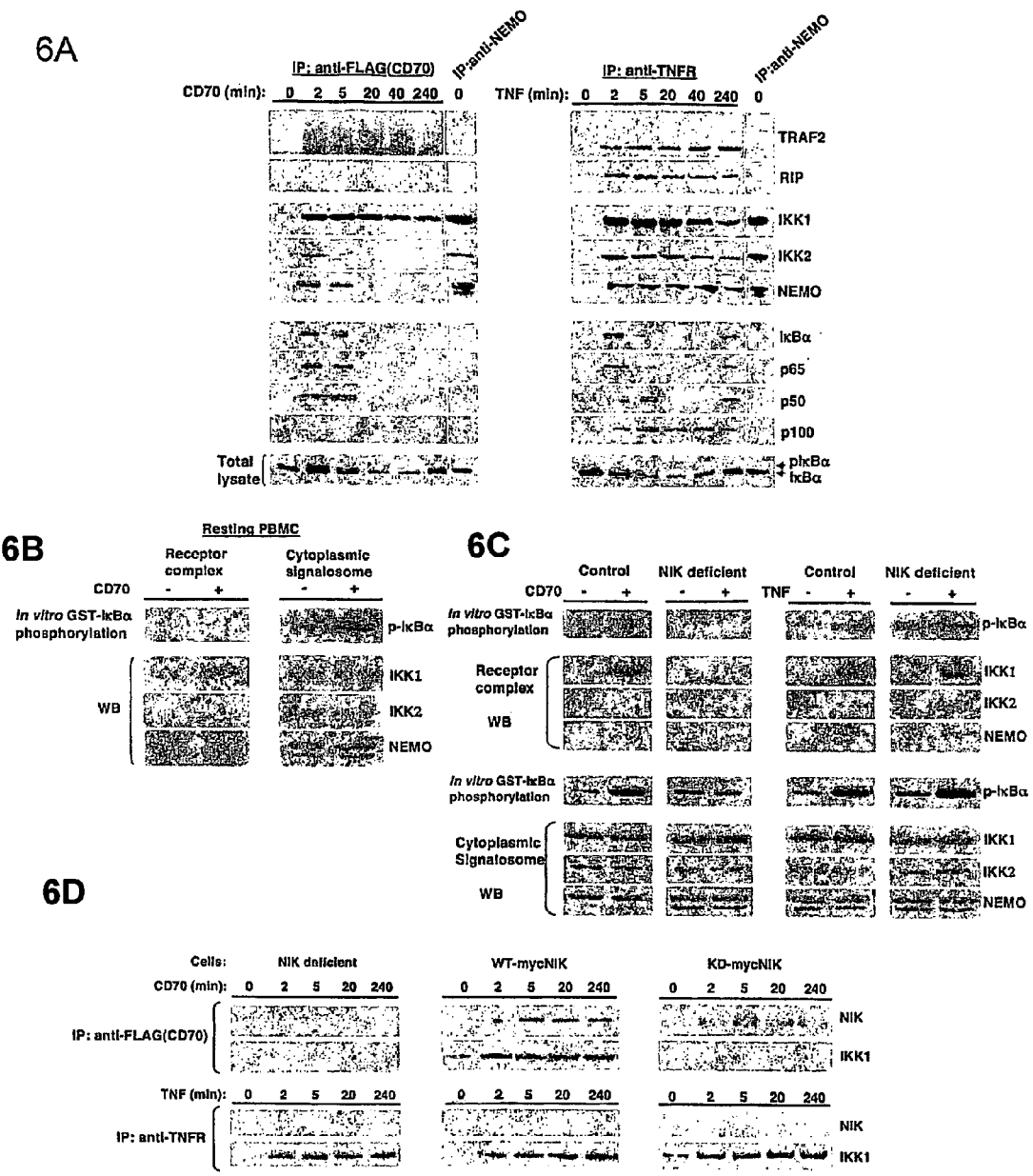

As used herein the phrase "immune disorder" refers to a disorder associated with insufficient of excessive antigen-specific or antigen non-specific (i.e., innate) immune response in which there is an abnormal activity of at least one protein (further described hereinbelow) participating in a NIK-dependent NF-κB signaling (i.e., canonical and alternative pathways, such as illustrated in FIG. 6). Examples of such disorders include, but are not limited to, multiple myeloma (MM), acquired immunodeficiency syndrome (AIDs), Sjogren's syndrome (SS), B-cells chronic lymphocytic leukemia (B-CLL), systemic lupus erythematosus, inflammatory colon disease, systemic inflammatory response syndrome (SIRS), multiple organ disinfection syndrome (MODS) and acute respiratory distress syndrome (ARDS), Addison's disease, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, rheumatoid arthritis, scleroderma, systemic anaphylaxis, systemic sclerosis, ulcerative colitis, Werner syndrome, and complications of cancer, hemodialysis, and extracorporeal circulation; viral, bacterial, fungal, parasitic, protozoal, and helminthic infections; and trauma.

As used herein the term "treating" refers to preventing, curing, reversing, attenuating, alleviating, minimizing, suppressing or halting the deleterious effects of an above-described immune disorder.

As used herein the term "individual" refers to a mammal, preferably a human.

According to the present invention, an individual can be provided with a therapeutically effective amount of an agent capable modulating the activity of a target gene or a target gene product (i.e., RNA or protein) participating in a NIK-dependent NF-κB signaling, thereby treating the immune disorder in the individual.

As used herein the phrase "modulating the activity" refers to increasing or decreasing an intrinsic catalytic activity (e.g., kinase activity of NIK), interacting activity (e.g., NIK-SIVA interaction as illustrated in Example 1 of the Examples section) or expression (e.g., NIK expression as illustrated in Example 2 of the Examples section) of the target gene or target gene product.

A number of genes and their products can be used as targets in accordance with the present invention (see FIG. 6). Examples of such target genes are listed below along with examples immune disorders involving same.

BLyS—BLyS binds the BAFF-receptor protein and promotes the survival of mature B-cells and B-cell Response. The protein is abundantly expressed in peripheral blood leukocytes and is specifically expressed in monocytes and macrophages. It is also found in the spleen, lymph node, bone marrow, T-cells and dendritic cells. The involvement of B lymphocyte stimulator (BLyS) in multiple myeloma (MM) was demonstrated in several aspects. MM cells were shown to express BLyS receptors and BLyS, in turn, was shown to modulate proliferative capacity and survival of MM cells. BLys protein was also found in the bone marrow of MM patients [Novak et al., Blood. Epub ahead of print (2003)]. BLyS levels together with globulin were also found to increase as HIV disease progresses [Rodriguez et al., AIDS. 17:1983-1985 (2003)]. The involvement of BLyS molecule in another autoimmune disease, Sjogren's syndrome (SS), was demonstrated by its ability to mediate polyclonal activation of B lymphocytes, and its role in the production of auto-antibodies. It was also shown that in human SS patients, the level of BLyS correlates with the level of auto-antibodies. Thus, BLyS may play a part in activating specific auto-reactive B cells and modulating the level of production of auto-antibodies which are the hallmark of the disease [Mariette et al., Ann. Rheum. Dis. 62:168-171, (2003)]. Another disease, in which BLyS was shown to play a role, is systemic lupus erythematosus. Over-expression of BLyS in mice leads to a systemic-lupus-erythematosus-like (SLE-like) disease. Over-expression of BLyS is also common in human SLE. Treatment of SLE-prone mice with a BLyS antagonist ameliorates disease progression and enhances survival [Stohl, Arthritis Res. Ther. 5:136-138, (2003)]. An effect of ByLS was demonstrated in B-cell chronic lymphocytic leukemia (B-CLL), a disease characterized by accumulation of CD5(+) B cells in the periphery and bone marrow. All B-CLL patient cells studied, expressed one or more of 3 known receptors for BLyS. B-CLL cells from a subset of patients aberrantly express BLyS and APRIL mRNA, whereas these molecules were not detectable in normal B cells. In addition, BLyS was found to protect B-CLL cells from apoptosis and to enhance cell survival [Novak et al., Blood. 100:2973-2979, (2002)]. Heterotrimeric of two proteins, APRIL and BLyS were found in serum samples from patients with systemic immune-based rheumatic diseases, implicating a role for these molecules also in rheumatic diseases [Roschke et al., J. Immunol. 169: 4314-4321, (2002)]. Thus, the present invention envisages down-regulation of BLys signaling through NIK-dependent NF-κB pathway to overcome the above-described immune disorders.

CD40L—This ligand can activate NIK-dependent NF-κB signaling (see Example 6 of the Examples section) through binding to the CD40 receptor. CD40L was shown to be involved in HIV infection. It was suggested that reversing the relative CD40L deficiency seen in HIV infection can facilitate immune restoration in AIDS [Kornbluth, J. Leukoc. Biol. 68:373-382, (2000)]. Thus, the present invention envisages up-regulation of CD40L signaling through NIK-dependent NF-κB pathway to overcome the above-described immune disorders.

CD27—Expression of CD27, by B-cell chronic lymphocytic leukemia (B-CLL) cells have been shown to influence clinical outcome of this disease [Bannerji and Byrd, Curr. Opin. Oncol. 12:22-29, (2000)]. CD27 was also shown to have heterogeneous expression in multiple myeloma patients. Low CD27 expression was found to correlate with patients with high-risk disease [Guikema et al., Br. J. Haematol. 121: 36-43, (2003)]. CD27 was also found in systemic lupus erythematosus patients in relation with lymphocytes count and disease course [Swaak et al., Clin. Rheumatol. 14:293-300, (1995)]. Thus, the present invention envisages selected up-regulation or down-regulation of CD27 signaling through NIK-dependent NF-κB pathway according to the immune disorder to be treated.

NIK—"NF-κB inducing kinase" binds SIVA, TRAF2, TRAF5, TRAF6, IKKA AND NF-kappa-B⁻2/P100. This protein is weakly expressed in the testis, small intestine, spleen, thymus, peripheral blood leukocytes, prostate, ovary and colon.

SIVA—Upregulation in CD27 and SIVA was demonstrated in renal dysfunction (e.g., ischemic and injured renal tissue). The expression of both proteins was seen in cell populations known to be undergoing death via apoptosis or necrosis [Schumer et al., Am. J. Pathol. 140:831-838, (1992); Shimzu and Yamanaka, Virchows Archiv. B Cell Pathol. 64:171-180; (1993), Basile et al., Am J. Physiol. 272: F640-F647, (1997)]. It was suggested that strategies directed at modifying CD27-mediated renal apoptosis will impact positively on the course of acute ischemic renal injury [Padanilam et al., Kidney Int. 54:1967-1975, (1998)]. Thus, the present invention envisages down-regulation of SIVA signaling through NIK-dependent NF-κB pathway to overcome the above-described renal disorders. SIVA interaction with the capsid protein VP2 of coxsackievirus B3 (CVB3) was shown to sustain CVB3-caused disease [Henke (2003) Clin. Exp. Med. 2(4):192-6]. Thus, the present invention envisages down-regulation of SIVA signaling through NIK-dependent NF-κB pathway to overcome viral disorders. Absence of SIVA-CD27 interactions was implicated in myelomagenesis, suggesting up-regulation of SIVA-CD27 signaling through NIK-dependent NF-κB pathway to overcome myelomagenesis [Katayama (2003) Br J Haematol. 120(2):223-34].

As mentioned hereinabove treating the immune disorder, according to the present invention, is effected by providing to the individual an agent which is capable of increasing (i.e., upregulating) or decreasing (i.e., downregulating) the activity of at least one target gene or gene product, such as described hereinabove.

An agent capable of upregulating expression of a target gene of the present invention may be an exogenous polynucleotide sequence designed and constructed to express at least a functional portion of the target gene of the present invention. Accordingly, the exogenous polynucleotide sequence may be a DNA or RNA sequence encoding a CD27 (GenBank Accession No. NM_001242), CD40L (GenBank Accession No. NM_000074), BLys (GenBank Accession No. NM_006573), SIVA (SIVA1 and SIVA2, GenBank Accession NO: NM_006427 and NM_021709, respectively), or NIK (GenBank Accession number NM_003954) molecule, capable of modulating the immune disorder.

Thus, for example, to express exogenous NIK in mammalian cells, a polynucleotide sequence encoding NIK (SEQ ID NO:1) is preferably ligated into a nucleic acid construct suitable for mammalian cell expression. Such a nucleic acid construct includes a promoter sequence for directing transcription of the polynucleotide sequence in the cell in a constitutive or inducible manner. A suitable promoter can be, for example, a promoter derived from Lentiviral vectors (e.g., pSUPER) which is capable of directing NIK expression in B lymphocytes (see Example 2). The nucleic acid construct of the present invention can further include additional polynucleotide sequences such as for example, sequences encoding selection markers or reporter polypeptides, sequences encoding origin of replication in bacteria, sequences that allow for translation of several proteins from a single mRNA (IRES) such as for directing the simultaneous expression of NIK and SIVA to obtain higher expression levels of each and as such higher NF-κB activation levels (see Example 1 of the Examples section), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

It will be appreciated that the nucleic acid construct can be administered to the individual employing any suitable mode of administration, such as described hereinbelow (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

An agent capable of upregulating a target gene of the present invention may also be any compound which is capable of increasing the transcription and/or translation of an endogenous DNA or mRNA encoding the a target gene of the present invention. For example, PHA can be utilized to increase CD27 and CD70. In addition Anti-CD2 and Anti-CD3 antibodies can be utilized to increase CD27 levels (de Jong et al) while CD40L expression can be utilized to increase CD70 levels (Hintzen et al)

Alternatively or additionally, upregulation may be effected by administering to the individual at least one target such, as described hereinabove. Such proteins can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the proteins of the present invention can be generated using recombinant techniques such as described for the large scale production of recombinant CD70 in HEK293T cells (see Example 2 of the Examples section which follows) and by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224: 838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that protein targets of the present invention can also be commercially obtained. For example, recombinant BAFF (Cat. No. PF088) and recombinant CD40L (Cat. No. PF091) are available from MERCK Biosciences.

As mentioned hereinabove, treatment of immune disorders according to the present invention can also be effected by down-regulating a target gene or product thereof, such as described hereinabove.

One example, of an agent capable of downregulating a target gene product of the present invention is an antibody or antibody fragment capable of specifically binding the target gene product and inhibit binding thereof to effector molecules. For example, antibodies directed at amino acid coordinates 624-947 of NIK (SEQ ID NO: 2), at amino acid coordinates 123-175 of SIVA1 (SEQ ID NO:3) or at amino acid coordinates 58-110 of SIVA2 (SEQ ID NO:4) will prevent NIK-SIVA complex formation to thereby reduce NF-κB signaling. Alternatively, the antibodies of the present invention may still retain binding of the target gene product to effector molecules thereof but inhibit catalytic activity of thereof. Such an antibody directed against phosphorylated NIK activation loop is described in Example 4 of the Examples section which follows.

Preferably, the antibody specifically binds at least one epitope of the target gene product. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 845-51 (1996); Neuberger, Nature Biotechnology 14: 826 (1996); and Lonberg and Huszar, Intern. Rev. Immunol. 13, 65-93 (1995).

Another agent capable of downregulating a target gene of the present invention is a small interfering RNA (siRNA) molecule.

RNA interference is a two step process; the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation.

An siRNA molecule capable of specifically hybridizing with the mRNA of NIK to arrest synthesis thereof is described in Example 2 of the Examples section which follows (SEQ ID NO:15).

For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating a target gene of the present invention is a DNAzyme molecule capable of specifically cleaving an mRNA transcript or DNA, sequence of the target gene of the present invention. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl. Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a target gene of the present invention can also be effected by using an antisense polynucleotide capable of specifically hybridizing with an mRNA transcript encoding the target gene product.

Design of antisense molecules which can be used to efficiently downregulate a target gene must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a target gene of the present invention is a ribozyme molecule capable of specifically cleaving an mRNA transcript encoding a target gene product. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of regulating the expression of a target gene in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo      3'--A    G    G    T
duplex     5'--A    G    C    T
duplex     3'--T    C    G    A
```

However, it has been shown that the A-AT and G-GC triplets have the greatest triple helical stability (Reither and Jeltsch, BMC Biochem, Sep. 12, 2002, Epub). The same authors have demonstrated that TFOs designed according to the A-AT and G-GC rule do not form non-specific triplexes, indicating that the triplex formation is indeed sequence specific.

Thus for any given sequence in the target gene regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

It will be appreciated that polynucleotides and polypeptides such as described hereinabove, can also be used to downregulate an activity of a target gene product.

Thus, for example, a NIK polypeptide or polynucleotide encoding same which includes the mouse naturally-occurring mutation, alymphoplasia (aly), can be used to down-regulate NIK dependent NF-κB signaling. This mutation is autosomal recessive and was shown to result in the systemic absence of lymph nodes and Peyer patches, disorganized splenic and thymic structures with immunodeficiency in mice carrying thereof [Shinkura (1999) Nature Genet. 22:74-77].

It will be appreciated that down-regulating polypeptides and polynucleotides encoding same can be characterized by a dominant negative function, essentially a dominant effect on the activity of the wild type target gene product. For example, a protein product of kinase defective NIK may bind effector proteins (e.g., SIVA), thus forming inactive complexes and inhibiting NIK dependent NF-κB signaling. Dominant negative mutants of NIK are well known in the art, see for example Hay (2003) Biochem. Biophys. Acta. 1642(1-2):33-44; and Chandrasekar (2003) Biochem. J. 373:547-58. A dominant negative molecule of IKKα which blocks NF-κB activation is described by Shikama (2003) Eur. J. Immnol. 33:1998-2006. A dominant negative molecule of TRAF-2 is described by Costabnzo (2003) J. Cell Physiol. 195:402-10.

Alternatively, an agent capable of downregulating a target gene of the present invention may also be any compound which is capable of decreasing the transcription and/or translation process or leveks of an endogenous DNA or mRNA encoding the a target gene product of the present invention. For example, PMA treatment may be used to CD27 mRNA levels as described in De Jonge 1991 infra.

It will be appreciated that additional agents (i.e., putative immune modulators) which may be used in the present invention can be identified by examining the ability thereof to increase or decrease NIK-dependent NF-κB signaling. Thus, for example, agents may be tested for their ability to increase or decrease NIK-SIVA complex formation, or NIK-dependent CD27 regulation, using cytological, genetical and/or biochemical methods which are well known in the art and described in Examples 1-3 of the Examples section, which follows.

Molecules/agents which can be used to modulate the activity of NIK may be screened (identified and/or selected) by contacting a cell with a ligand of a TNF/NGF receptor family capable to induce NIK-dependent canonical and alternative pathway in the cell, incubating the cell prior to, after, or during said contacting with individual tested molecules, detecting activation of the canonical pathway in the cell and selecting individual molecule/s capable of modulating induction of the canonical pathway induced by said ligand.

In a preferred embodiment, CD70, CD40L, or Blys/BAFF ligand is used for the screening of molecules. Alternatively, new ligands capable to induce NIK dependent canonical and alternative pathway can be identified, as exemplified below for CD70.

The detection of canonical pathway activation, for the screening of the molecules, can be carried out by monitoring parameters indicative of the canonical pathway such as IκB degradation, IκBα phosphorylation and p65 translocation.

In a preferred embodiment of the invention, lymphoblastoid cell type such as Ramos, Raji and BJAB cells are used for the screening of the molecules of the invention.

In addition molecules/agents which can be used to modulate the activity of NIK may be screened by contacting a lymphoblastoid cell with a ligand of a TNF/NGF receptor family capable of activating NIK and the canonical pathway in the cell, incubating the cell prior to, after, or during said contacting, with individual tested molecules, detecting activation of the canonical pathway and, selecting individual molecule/s capable of modulating induction of the canonical pathway induced by said ligand but not by any other ligand capable of inducing canonical pathway in a NIK independent manner, such as TNF.

The agents of the present invention can be administered to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al;, "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

NIK-SIVA Binding

The binding of NIK to SIVA and the effect of their co-expression were tested using binding, co-expression and immunoprecipitation assays.

Antibodies:

Anti-HIS antibody was purchased from Sigma. Anti-myc monoclonal antibody (clone-9E10) was purified from mouse ascitic fluid on a myc-peptide affinity column.

Cells:

HEK293T cells were cultured in Dulbecco's modified Eagle's minimal essential medium supplemented with 10% fetal calf serum, 100 U/ml penicillin and 100 µg/ml streptomycin.

Expression Vectors:

A vector for expressing NIK (SEQ ID NO:1) N-terminally fused to the myc tag (EQKLISEEDL, SEQ ID NO:5) was obtained from Dr. Michael Kracht, Germany. The cDNAs for human SIVA1 (SEQ ID NO:6) and SIVA2 (SEQ ID NO:7) were PCR-amplified from ESTs and cloned into the pcDNA3.1-HIS vector (Invitrogen). pEGFP plasmid was purchased from Clontech. Human NIK with a mutation corresponding to that of the mouse aly mutation (G860R) (Shinkura et al., 1999; NM_016896) was generated with a site-directed mutagenesis kit (Stratagene), using (sense) 5' CCAAGCTATTTCAATCGTGTGAAAGTCCAAATAC (SEQ ID NO:8) and (antisense) 5' GTATTTGGACTTTCA-CACGATTGAAATAGCTTGG (SEQ ID NO:9).

Yeast Two-hybrid Screening:

A BamHI/XhoI digested NIK insert from the pcNIK vector was subcloned into BamHI/SalI sites of the Gal4 DNA-binding domain vector pGBKT7 (Clontech). A pre-transformed human bone marrow library (HL4053AH, Clontech) was subjected to two-hybrid screening using pGBKT7-NIK as the bait, according to the manufacturer's instructions (Yeast protocol handbook, Clontech—www.clontech.com) Positive clones were identified by quadruple selection and β-galactosidase activity assay. Binding of the SIVA clone to NIK and NIK624-947 was reconfirmed and binding of NIK to TRAF2 was assessed-by a β-galactosidase expression assay using the yeast SFY526 reporter strain (Clontech) and the pGBKT7 and pGADT7 vectors.

Transfections, Immunoblotting and Immunoprecipitations:

For co-immunoprecipitation of transfected proteins, HEK293T cells were seeded onto 90-mm plates ($1.5 \times 10^6$ cells/plate) and transfected using the calcium phosphate precipitation method (Sambrook et al., 1989) a day later using a total amount of 10 µg DNA in 10 ml of DMEM medium with 10% FBS. For co-transfection a 1:1 mixture of the plasmids encoding tested proteins was used. Twenty four hours following transfection the cells were rinsed once with phosphate buffered saline (PBS) and lysed in 1 ml of lysis buffer (10 mM Tris-HCl (pH 7.6), 250 mM NaCl, 1% NP-40, 1 mM EDTA, 1 mM PMSF) which included 1× complete protease inhibitor cocktail (Roche Molecular Biochemicals). Pre-cleared lysates were incubated for 2 hours at 4° C. with 2 µg of anti-myc or anti-HIS antibody preadsorbed to protein-G-Sepharose beads (Amersham biosciences). The beads were then rinsed with lysis buffer, subjected to SDS-PAGE, and the proteins were transferred to a nitrocellulose membrane and probed with the indicated antibodies. The antibodies were visualized with horseradish peroxidase (HRP)-coupled secondary antibodies, using the enhanced chemiluminescence (ECL) western blotting detection system (Amersham) according to the manufacturer's instructions.

Reporter Gene Test:

NIK-mediated NF-κB activation was measured by reporter gene assay. HEK293T cells ($1.5 \times 10^5$/well) were seeded onto 6-well plates and transfected by the calcium phosphate precipitation method (Sambrook et al., 1989) one day later. For co-transfection, a 1:1 mixture of the plasmids encoding the tested proteins was used. To maintain total DNA concentration at 2 μg/well, a pcDNA3 (Invitrogen) 'empty' vector was added. Twenty-four hours following transfection, the cells were harvested, lysed, and reporter gene activity was determined using the luciferase assay system (Promega).

NIK Binds to SIVA, an Adapter Protein Associated with CD27:

Screening of a human bone marrow two-hybrid library using NIK as bait uncovered that NIK specifically binds a C-terminal portion of a protein termed SIVA which was previously shown to associate with CD27, a receptor of the TNF/NGF family expressed mainly in T and B lymphocytes (Prasad et al., 1997). As with binding of TRAF to NIK (Malinin et al., 1997), the present study demonstrated that the C-terminal portion of SIVA binds the C-terminal portion of NIK and that this binding was stronger when the respective portions and not the whole protein was utilized in the binding assays (FIG. 1a). This is probably due to the propensity of the N-terminal part of NIK to bind to its own C-terminus and thus block binding of this portion with other proteins (Xiao and Sun, 2000).

Co-expression of NIK with SIVA1 or SIVA2, the two known SIVA splice variants (Yoon et al., 1999), in transiently transfected HEK293 cells revealed that NIK can bind SIVA in mammalian cells. As shown in FIGS. 1b-c, NIK co-immunoprecipitated bidirectionally with both splice variants from lysates of the transfected cells. The quantity of SIVA1 or SIVA2 in the transfected cells increased when co-expressed with NIK, apparently reflecting stabilization of SIVA by its associated NIK molecules. The expression of NIK was also enhanced by the co-expression of either of the two SIVA splice variants (FIGS. 1b, 1c). No such enhancement was observed upon co-expression of NIK with green fluorescent protein (GFP) or IKK1 (FIG. 1d). Expression of SIVA2 did not increase the quantity of co-expressed NIK containing an inactivating missense mutation corresponding to that found in the aly mice (G860R), even though this NIK mutant did co-immunoprecipitate with SIVA1 and to some extent also with SIVA2 (FIGS. 1b-c).

SIVA also appeared to be capable of affecting NIK function. When expressed alone, SIVA1 or SIVA2 caused only slight activation of NF-κB. However, both splice variants significantly enhanced the activation of NF-κB by co-expressed NIK while not affecting the activation of NF-κB by the co-expressed NIK aly mutant (FIG. 1e).

Example 2

CD27 Induces Processing of Both IκB and NF-κB2/p100 in Lymphocytes, While Arrest of NIK Synthesis in Ramos Lymphoblastoid Cells Blocks CD27-Induced NF-κB Activation The ability of CD70 (CD27 ligand) to induce processing of both IκB and NF-κB2/p100 in lymphocytes was determined via western blot analysis which utilized antibodies directed against p100, p52, RelB, IκBα and p65. The effect of the presence of NIK in these cells on the induced processing was assessed by western blot analysis of the same molecules on NIK suppressed cells.

Reagents:

CD70 (GenBank Accession number Y13636) was produced by large-scale transfection of human embryonic kidney (HEK) 293T cells with the relevant expression constructs (see below). MG132 was purchased from Calbiochem. Ficoll-Paque was purchased from Amersham Biosciences. G418 was purchased from Life Technologies. Phytohemagglutinin (PHA) was purchased from Sigma. In all tests, the conditioned medium of the transfected cells was used at a dilution of 1:4.

Antibodies:

Anti-p52 antibody was purchased from Upstate Biotechnologies, antibodies against p65, RelB, CD27 and Lamin A/C from Santa Cruz Biotechnology, anti-IκBα from Transduction Laboratories, anti-myc monoclonal antibody was purified as described in Example 1. The anti-NIK monoclonal antibody NIK-81 was raised by immunizing mice with a KLH-coupled peptide corresponding to a sequence within the NIK kinase domain (RLGRGSFGEVHRMEDK, SEQ ID NO:10) which included a cysteine at the N terminus for coupling. Anti-NIK monoclonal antibody was purified on affigel (BIORAD), an affinity column to which the BSA linked peptide was coupled.

Cells:

Human peripheral blood mononuclear cells (PBMC) were isolated from buffy coat samples by Ficoll-Paque gradient centrifugation at 450×g. Cells were subjected to stimulation with CD70 without any pretreatment or following their activation for 48 hours with 1 μg/ml PHA that was followed by a 12 h resting period without PHA. The PBMC, as well as cells of the human B lymphoblastoid lines of Burkitt lymphoma origin, Ramos (Benjamin et al., 1982), Raji (Pulvertaft, 1964), were cultured in RPMI medium supplemented with 10% fetal calf serum, 100 U/ml penicillin and 100 μg/ml streptomycin. HEK293T cells were cultured as described in Example 1 of the Examples section.

Expression Vectors:

The cDNAs for the extracellular domains of mCD70, was PCR-amplified from ESTs and cloned in fusion with a modified leucine zipper and FLAG tag (Fanslow et al., 1994) into pcDNA3 (Invitrogen). The cDNA corresponding to the full-length NIK was cloned into the Gal4 DNA-binding domain vector pGBKT7 (Clontech). NIK which sequence was altered to make it non-complementary to the NIK siRNA, was generated using (sense) 5'GAGGGTCTGGAATACCTACAT-TCCCGCAGGATTCTGCATGGG (SEQ ID NO:11) and (antisense) 5'CCCATGCAGAATCCTGCGGGAATGTAG-GTATTCCAGACCCTC (SEQ ID NO:12), as primers.

siRNA and Lentiviral Transduction:

Hairpin siRNA was expressed using the pSUPER vector, as previously described (Brummelkamp et al., 2002). Briefly, a double-stranded oligonucleotide was designed to contain the forward and reverse sequences corresponding to a region in the human NIK open reading frame (nucleotides 1513-1531) linked by a 9-base-pair spacer region (ttcaagaga SEQ ID NO:15): sense strand 5'gatccccTACCTCCACTCACGAAG-GAttcaagagaTCCTTCGTGAGTGGAGGTAttttttggaaa (SEQ ID NO:13); antisense strand 5'agcttttccaaaaaTACCTC-CACTCACGAAGGAtctcttgaaTCCT-TCGTGAGTGGAGGTAggg (SEQ ID NO:14). The two oligonucleotides were annealed and cloned into the BglII and HindIII (Brummelkamp et al., 2002) sites of the pSUPER vector for expression under the control of the H1 RNA promoter (Brummelkamp et al., 2002). Transient transfection with up to 5-fold excess of this pSUPER-NIK over co-transfected NIK was performed, as described above.

A lentiviral vector (Lois et al., 2002) was used in order to express the pSUPER-NIK constitutively in Ramos cells. The cassette including the H1 promoter (Brummelkamp et al., 2002) and NIK RNAi was excised from the pSUPER vector using EcoRI and HindIII (both from New England Biolabs), the sticky ends were blunted using T4 DNA polymerase (New England Biolabs), and the blunted fragment was inserted into the blunted PacI site of the GFP-expressing FUGW lentiviral vector (Lois et al., 2002). Transduced cells were sorted by FACS for GFP expression (FACS Vantage, Becton-Dickinson); Sorted cells exhibited expression of GFP and deficiency of NIK for months.

Transfections, Immunoblotting and Immunoprecipitations:

Transfections, immunoblotting and immunoprecipitations were performed as described in Example 1 of the Examples section.

Ramos cells ($2-4\times10^8$; $1\times10^8$ cells/ml) were lysed and immunoprecipitated with affinity-purified mouse anti-NIK antiserum coupled to protein-G-Sepharose beads in order detect endogenous NIK. The precipitated protein was detected by western blotting using the NIK-81 antibody and the SuperSignal West Femto Chemiluminescent Detection Kit (Pierce).

For immunoprecipitation of the NF-κB proteins, nuclear extracts from $10-20\times10^6$ cells were diluted to achieve the following composition: 0.5% NP-40, 10 mM HEPES pH 7.9, 150 mM NaCl, 1 mM EDTA, 1 mM EGTA, 1 mM dithiothreitol (DTT), 1 mM PMSF, and 1× complete protease inhibitor cocktail. Anti-RelB antibody preadsorbed to protein-A-Sepharose beads (Amersham Biosciences) was incubated with precleared nuclear lysates for 2 hours at 4° C. The immunoprecipitates were analyzed by SDS-PAGE using 4-12% Bis-Tris NuPAGE gels (Invitrogen), and the gels were subjected to western blotting as described above.

Ligand activation of lymphoid cell lines and PBMC, was typically carried by stimulating $1\times10^6$ cells for the time periods indicated in the figures (0, 0.3 and 4 hours or 0, 1 and 4 hours; FIG. 2a-b) with the relevant ligands, and nuclear and cytoplasmic extracts were prepared as described (Schreiber et al., 1989) and analyzed by western blotting.

Ligand activation of Raji cells was carried by stimulating cells for the time periods indicated in the figures (0, 0.3 and 4 hours or 0, 1 and 4 hours; FIG. 2a-b) with CD70. Ligand activation of normal and $NIK^{(MINUS)}$ Ramos cells was carried by stimulating cells for the time periods indicated in the figures (0, 0.3, 1, 4 and 20 hours; FIGS. 2d-e or 0, 0.15, 0.3, 4 and 16 hours; FIG. 2h) with CD70.

Reintroduction of NIK to the $NIK^{(MINUS)}$ cells was performed by nucleotransfection of $NIK^{(MINUS)}$ cells with the expressing vector using the Nucleofector Kit V according to the manufacturer's instructions (Amaxa Biosystems). Briefly, $2\times10^6$ $NIK^{(MINUS)}$ cells were nucleofected with 4 μg of mutated myc-tagged NIK plasmid and 1 μg of pcDNA3 in solution V using the program S18 in the Nucleofector device. Cells stably expressing the transfected protein were selected on G418 (1 mg/ml).

Protein Kinase C Assay:

PKC activity in control and NIK deficient Ramos cells was measured (0, 15 and 30 minutes) following CD70 stimulation by using the Signatect Protein Kinase C assay system (Promega). The enzymatic activity of PKC was determined by subtracting the values obtained when assaying in the absence of phospholipids from those obtained in their presence.

CD27 Induces Processing of Both IκB and NF-κB2/p100 in Lymphocytes:

The ability of NIK to bind to SIVA suggested that NIK might play a role in the cellular function of CD27. Therefore, the effects of CD27 on the alternative NF-κB activation pathway in which NIK function has been implicated was examined.

Treatment of human peripheral blood mononuclear leukocytes (PBMC) with the CD27 ligand, CD70, induced rapid decrease of IκBα (FIGS. 2a, 2b, top panels), indicating that the receptor can trigger activation of the canonical NF-κB pathway. This decrease was easier to detect in activated PBMC, in which the basal IκBα level is high (FIG. 2b, top panel), but on careful examination it could also be discerned in non-stimulated PBMC, which contain much less IκBα (FIG. 2a, top panel). In resting PBMCs, CD70 also induced translocation of NF-κB2/p52 (p52) as well as of RelB to the nuclei, indicating that CD27 stimulates the alternative NF-κB pathway in these cells as well (FIG. 2a, bottom panel). Following PHA activation, which results in increased expression of both CD27 and CD70 in PBMC (de Jong et al., 1991 and Hintzen et al., 1994), the basal nuclear level of both p52 and RelB was very high, preventing the assessment of the effect of applied CD70 on p52 generation (FIG. 2b, bottom panel).

The present study also showed that CD70 induces IκBα degradation as well as nuclear translocation of RelB and NF-κB2/p52 in Ramos and Raji lymphoblastoid lines (FIG. 2c and left panels in FIGS. 2d, 2e). Treatment of Raji cells with CD70 induces IκBα degradation within 20 minutes of CD70 application while later on IκBα levels increased. IκBα degradation was associated with nuclear translocation of p65, RelB and NF-κB2/p52 (FIG. 2c).

Similar pattern of IκBα degradation was observed in Ramos cells following CD70 application (FIG. 2e, left panel). IκBα degradation was associated with a prolonged increase in nuclear p65 levels (FIG. 2e, left panel). On the other hand, the nuclear translocation of RelB occurred rather slowly, reaching maximal translocation about 4 hours following CD70 application (FIG. 2d, left panel). Nuclear translocation of p52 started within the first 20 minuets and was maintained for 20 hours. Accumulation of p100 in the nuclei of Ramos cells appeared within the first hour (FIG. 2d, left panel), a process that was suggested to reflect induced translocation of this protein in association with RelB to the nucleus (Yilmaz et al., 2003).

Arrest of NIK Synthesis in Ramos Lymphoblastoid Cells Blocks CD27-Induced Activation of Both the Canonical and the Alternative NF-κB Pathways:

To examine the role of NIK in activating various NF-κB forms through CD27, NIK synthesis in Ramos cells was arrested by infecting these cells with a lentiviral vector expressing a hairpin short interfering RNA (siRNA) capable of blocking NIK synthesis. Western analysis confirmed that both in transient and stable expression scenarios, the siRNA vector effectively arrested the synthesis of NIK (FIG. 2f, top and middle panels). As expected from the reported participation of NIK in the NF-κB alternative pathway, treatment of the $NIK^{(MINUS)}$ Ramos cells with CD70 failed to induce translocation of p52 or of RelB to their nuclei. The translocation of p100 induced by CD70 in these cells was also significantly delayed (FIG. 2d, right panel). NIK deficiency also resulted in inability of CD70 to induce IκBα degradation or nuclear p65 translocation (FIG. 2e, right panel), both manifestations of the canonical pathway.

Control tests confirmed that the NIK$^{(MINUS)}$ Ramos cells express CD27 at levels comparable to those of normal Ramos cells and thus exhibit normal protein kinase C (PKC) activation upon CD27 triggering (Erlichman and Howard, 1999) (FIG. 2g and its inset). These results indicated that the inability of NIK$^{(MINUS)}$ Ramos cells to activate NF-κB was not caused by aberrant CD27 function. To verify this observation, NIK expression was reinstated to the NIK$^{(MINUS)}$ cells (FIG. 2f, bottom panel) by transfecting these cells with myc-tagged NIK cDNA to which conservative sequence changes were introduced to make it non-complementary with the NIK siRNA sequence. Although the IκBα and nuclear p52 levels in these cells were somewhat higher than normal (probably due to spontaneous NIK signaling as a result of its supranormal expression level), the NIK$^{(MINUS)}$ reconstituted cells regained the ability to respond to CD70 with both an increase in nuclear p52 and a transient decrease in IκBα (FIG. 2h), further confirming the pivotal-role of NIK in activation of both the alternative and the canonical NF-κB pathways.

Example 3

The Effect of NIK Suppression on the Canonical and the Alternative NF-κB Pathways The ability of CD40, BLyS, TNF, thapsigargin, or PMA to induce the canonical and the alternative NF-κB pathways was determined via western blot analysis which utilized antibodies directed to p100 p52, RelB, IκBα and p65. The effect of the presence of NIK in the cells was assessed by western blot analysis of the same molecules on NIK suppressed cells.

Reagents:

Production of hCD 154 (CD40L) and hBLyS/BAFF was carried by large-scale transfection of human embryonic kidney (HEK) 293T cells with the relevant expression constructs (see below). In all tests, the conditioned media of the transfected cells were as described in Example 2. TNF, a gift from Dr. G. Adolf, Boehringer Institute, Vienna, Austria, was applied to cells at a concentration of 50 ng/ml. Thapsigargin, 4β-phorbol-12-myristate-13-acetate (PMA), and phytohemagglutinin (PHA) were purchased from Sigma.

Antibodies:

The source of antibodies against p65, RelB, p52, p100, IκBα is described in Example 2 of the Examples section. Anti c-Rel was purchased from Santa Cruz Biotechnology. Anti-β actin and anti-FLAG were purchased from Sigma. Anti-phospho-IκBα was purchased from Cell Signaling Technology.

Cells:

Ramos (Benjamin et al., 1982) cells were cultured as described in Example 2 of the Examples section.

Expression Vectors:

The cDNAs for the extracellular domains of hCD154 (CD40L) (ATCC clone 79814), and hBLyS/BAFF (Resgen clone 631119) were PCR-amplified from ESTs and cloned in fusion with a modified leucine zipper and FLAG tag (Fanslow et al., 1994) into pcDNA3 (Invitrogen). NIK suppression was generated as described in Example 2 of the Examples section.

Transfections, Immunoblotting and Immunoprecipitations:

Transfections, immunoblotting and immunoprecipitations were performed as described in Example 1 of the Examples section. Phosphorylated IκBα was detected after pretreatment (2 h) with the proteasomal inhibitor MG132 (25 μM).

Ligand activation of normal and NIK$^{(MINUS)}$ cells was carried by stimulating cells for the time periods indicated: 0, 0.2, 0.5, 1 and 16 hours (FIG. 3a), 0, 0.25, 1 and 16 (FIG. 3a-b) with CD40L, for time periods of 0.3, 4 and 20 hours (FIG. 3c-d) with BLyS, for time periods of 0, 0.3, 4 and 20 hours (FIG. 3e) or 0, 0.3, 1, 4 and 20 hours (FIG. 3f) with TNF. Cells stimulation by CD70 and TNF was carried for 0, 15 minutes and 4 hours (FIG. 3g). Stimulation by Thapsigargin and PMA was carried for 0, 30 minutes and 4 hours (FIG. 3h).

Studies of the effects of various ligands of the TNF family on NF-κB activation in lymphocytes have demonstrated activation of both the canonical and the alternative NF-κB pathways by two ligands, the CD40 ligand (CD40L) (Berberich et al., 1994) (Coope et al., 2002) and BLyS/BAFF (Claudio et al., 2002) (Kayagaki et al., 2002) (Hatada et al., 2003). On the other hand, TNF, though capable of effectively triggering the canonical pathway, appears unable to trigger the alternative pathway (Matsushima et al., 2001) (Yin et al., 2001) (Dejardin et al., 2002) (Yilmaz et al., 2003). TNF, induces only a slight increase in nuclear p52, much less than that induced by ligands such as CD40L (Yilmaz et al., 2003) (Derudder et al., 2003), probably through stimulating the synthesis of p100 (de Wit et al., 1998). TNF also induces synthesis of RelB (Bren et al., 2001), which in part accumulates in the nucleus apparently through induced nuclear translocation of p100:RelB dimers (Yilmaz et al., 2003).

The responses of the Ramos cells to CD40L, BLyS/BAFF, and TNF in the present study were consistent with those reports. All three ligands induced activation of the canonical pathway, as reflected in rapid nuclear translocation of p65 (FIGS. 3b, 3d, 3f, left panels). This translocation was associated with a decrease in IκBα (FIGS. 3b, 3f, left panels) or, in the case of BLyS/BAFF induction, phosphorylation of IκBα with no visible change in its cellular levels was detected (FIG. 3d, left panel). CD40L and BLyS/BAFF also induced marked increase in nuclear p52 as well as in RelB, both reflecting activation of the alternative pathway (FIGS. 3a, 3c, left panels). TNF induced nuclear translocation of RelB, but only a slight increase in nuclear p52 (FIG. 3e, left panel). Assessment of co-immunoprecipitation of various NF-κB proteins from nuclear extracts of Ramos cells confirmed that whereas CD70 enhances nuclear accumulation mainly of RelB:p52 but also of RelB:p100, TNF induces increased nuclear levels of RelB:p100 without increasing RelB:p52 (FIG. 3g).

The induction of the NF-κB pathway by CD40L, BLyS/BAFF, TNF, thapsigargin and PMA was tested in Ramos cells in which NIK expression was arrested. All effects of CD40L and BLyS on NF-κB activation (nucleus translocation of p100, p52, RelB and p65 as well as IκBα degradation in the cytoplasm) were arrested in the NIK$^{(MINUS)}$ Ramos cells (FIGS. 3a-d, right panels). In contrast, the induction of IκBα degradation by TNF and the resulting nuclear translocation of p65, as well as the induction of nuclear translocation of p100 and RelB, occurred in the NIK$^{(MINUS)}$ cells just as effectively as in the cells expressing NIK (FIGS. 3e, 3f, right panels). NIK depletion also had no effect on IκBα degradation in response to thapsigargin, an inhibitor of the sarco-endoplasmic reticulum Ca$^{2+}$-adenosine triphosphatase that triggers activation of NF-κB through induction of endoplasmic reticulum stress (Pahl and Baeuerle, 1996), or to 4β-phorbol-12-myristate-13-acetate (PMA), an agent activating NF-κB through stimulation of PKC (Sen and Baltimore, 1986) (FIG. 3h).

Besides the loss of unresponsiveness to the effects of CD70, CD40, and BLyS/BAff on NF-κB, the NIK$^{(MINUS)}$ Ramos cells also displayed some constitutive alterations of their basal NF-κB protein levels. They showed marked reduction of basal p52 and a significant decrease in RelB and c-Rel, as well as some reduction of p100 and IκBα (FIGS. 3e, 3f and 3i). Expression of all the above proteins depends in part on NF-κB activation (Hannink and Temin, 1990; Ten et al., 1992; Lombardi et al., 1995 and Bren et al., 2001). p65, whose expression is independent of NF-κB (Ueberla et al., 1993), occurred in the NIK$^{(MINUS)}$ cells in normal amounts (FIG. 3i), although its basal nuclear level was reduced (FIG. 2e). These constitutive alterations in the levels of NF-κB proteins in the NIK$^{(MINUS)}$ cells are reminiscent of those observed in lymphocytes of the aly mice (Yamada et al., 2000). They probably reflect arrest of the effects of some autocrine mediator(s) that continuously activate NF-κB to a slight extent, in a NIK-dependent manner.

Example 4

The Effect of Antibodies Against the Phosphorylated Activation-Loop of NIK on IκKα Degradation Antibodies against the phosphorylated activation-loop of NIK (αp-NIK) were introduced into Ramos and BJAB cells creating instantaneously ablation of NIK activation. The effect of these antibodies on the induction of IκBα degradation by CD70 and CD40L and TNF was measured.
Reagents:
CD70 was produced as described in Example 2 of the Examples section. CD40L was produced as described in Example 3 of the Examples section. TNF was obtained as described in Example 3 of the Examples section. [γ$^{32}$P]ATP was purchased from Amersham Biosciences.
Antibodies:
The IκBα antibody is described in Example 2 of the Examples section. Anti-myc monoclonal antibody was purified as described in Example 1 of the Examples section. A monoclonal antibody against the phosphorylated NIK activation loop (α-pNIK) was raised by immunizing mice with a KLH-coupled peptide corresponding to the NIK activation loop in which Thr559 was phosphorylated. The anti-NIK monoclonal antibody NIK-81 was raised as described in Example 2 of the Examples section. Both anti-NIK monoclonal antibodies were purified on affinity columns to which their corresponding peptides were coupled.
Cells:
The Ramos cells and HEK293T cells are described in Example 1 of the Examples section. BJAB cells (Clements et al., 1975) were cultured in RPMI medium supplemented with 10% fetal calf serum, 100 U/ml penicillin, and 100 µg/ml streptomycin.
Expression Vectors:
The cDNAs for the extracellular domains of CD70 was cloned as described in Example 2 of the Examples section. hCD154 (CD40L) and hBLyS/BAFF were cloned as described in Example 3 of the Examples section.
Transfections, Immunoblotting and Immunoprecipitations:
Transfections, immunoblotting and immunoprecipitations were performed as described in Example 1 and Example 2 of the Examples section.
Antibody Transfection:
Antibodies were transfected into cells in serum-free medium using the Project Protein Transfection Reagent Kit (Pierce), according to the manufacturer's instructions. Ligands were applied, in regular (serum-containing) medium (RPMI1640 WITH 10% FBS), 3-4 hours following antibody transfection.
Assessment of Uptake of FITC-Tagged Immunoglobulin:
Assessment of FITC-tagged immunoglobulin uptake was carried via fluorescence microscopy 0, 1, 4 and 8 hours after transfection.

NIK activation was instantaneously ablated in order to exclude the possibility that the differences in ligand effects observed between the NIK$^{(MINUS)}$ and the normal cells are secondary to such constitutive alterations occurring in the cells as a consequence of prolonged NIK deficiency. NIK activation involves phosphorylation of its activation loop (Lin et al., 1998). A monoclonal antibody that was raised against a phospho-peptide corresponding to the phosphorylated NIK activation loop (α-pNIK) and introduced into Ramos cells was shown to effectively block the in-vitro kinase function of NIK in a dose dependent-manner (FIG. 4a, top panel). FIG. 4b illustrates that treatment of Ramos cells with a protein-transfection kit allowed effective, though transient, introduction of immunoglobulins into the cells. Introduction of the α-pNIK antibodies into Ramos cells had no effect on the induction of IκBα degradation by TNF. However, the antibodies effectively blocked the induction of IκBα degradation by CD70 or CD40L (FIG. 4c). In BJAB cells, CD40L induced IκBα degradation and this induction was significantly reduced when the α-pNIK antibodies were introduced (FIG. 4d). These findings further confirm that although NIK does not participate in activation of the canonical pathway by TNF, its function in lymphocytes is crucial for activation of the canonical pathway by other ligands.

Example 5

The Effect of CD70 on Activation of the Canonical Pathway

The abilities of TNF and CD70 to activate the IKK signalosome were compared. Their effect on the mechanisms of canonical pathway was examined in control and NIK deficient cells. The effect of the presence of NIK in the cells was assessed by western blot analysis of the same molecules on NIK suppressed cells.
Reagents:
CD70 is described in Example 2 of the Examples section, TNF is described in Example 3 of the Examples section.
Antibodies:
Anti-myc was purified as described in Example 1 of the Examples section. Anti-IκBα and anti-NIK (NIK-81) are described in Example 2 of the Examples section. Anti-phospho-IκBα is described in Example 3 of the Examples section. Antibody against the phosphorylated NIK activation loop (α-pNIK) is described in Example 4 of the Examples section. Anti-FLAG M2-beads were purchased from Sigma. IKKα (M280 & H744) from Santa Cruz Biotechnology, anti-IKKβ and anti-IKKγ from BD-Pharmingen.
Cells:
Ramos cells and PBMC cells are described in Example 2 of the Examples section.
Expression Vectors:
GST-IκBα was a gift from Signal pharmaceuticals. NIK suppressing vectors are described in Example 2 of the Examples section.
Transfections, Immunoblotting and Immunoprecipitations:
Transfections, immunoblotting and immunoprecipitations were performed as described in Example 2 and Example 3 of the Examples section. For immunoprecipitation of the CD70/CD27 ligand-receptor complexes from resting PBMC and Ramos cells, cell lysates were prepared as described for the kinase tests aforementioned and incubated for 4 hours at 4° C. with 25 µl of 50% M2-FLAG agarose beads per ml of lysate. The TNF-receptor complex was precipitated as described (Zhang et al., 2000). The signalosome from cell lysates was immunoprecipitated using a 1:1 mixture of two different antibodies against IKK1 (M-280 and H-744, Santa Cruz). Immunoprecipitation was allowed to continue for 2 hours at 4° C., using 10 µg of anti-IKKα antibodies adsorbed to 25 µl of 50% protein-A-Sepharose beads per ml of lysate.

In vitro GST-IκBα phosphorylation in normal and NIK$^{(MINUS)}$ Ramos cells was carried by stimulating cells for the time periods indicated (0, 0.25 and 4 hours) (FIG. 5a) with CD70 or TNF.

Kinase Tests:

The in-vitro IKK kinase activity of the receptor complexes and cytoplasmic signalosome complex, using a bacterially expressed GST-IκBα (1-54) (Uhlik et al., 1998 and Dejardin et al., 2002)) as substrate, was assessed as previously described (Uhlik et al., 1998 and Dejardin et al., 2002). Briefly, 2-4×10$^8$ Ramos cells were lysed by rotation for 30 minutes at 4° C. in lysis buffer (20 mM HEPES pH 7.6, 250 mM NaCl, 0.5% NP-40, 20 mM β-glycerophosphate, 1 mM EDTA, 20 mM p-nitrophenyl phosphate, 0.1 mM sodium vanadate, 2 mM sodium fluoride, 1 mM DTT, 1 mM PMSF, and 1× complete protease inhibitor cocktail). Cellular debris was removed by centrifugation at 10,000×g and the lysate was pre-cleared with protein A/G beads on to which rabbit/mouse pre-immune serum was adsorbed, and then subjected to immunoprecipitation for 2 hours at 4° C. The immunoprecipitates were washed four times with lysis buffer and twice with kinase buffer (20 mM HEPES pH 7.6, 20 mM MgCl$_2$, 20 mM β-glycerophosphate, 1 mM EDTA, 2 mM p-nitrophenyl phosphate and 2 mM DTT). The kinase reaction was allowed to proceed by incubating the immunoprecipitated proteins bound to 20-µl beads in kinase buffer (40 µl) containing 1 µg GST-IκBα (1-54) and 5 µci [γ$^{32}$P]ATP at 30° C. for 30 minutes. The kinase activity of NIK was assessed under the same conditions, using myc-tagged NIK that had been over-expressed in transfected HEK293T cells and immunoprecipitated using anti-myc antibody. The kinase test was carried out in the presence of α-pNIK or IgG as control, following pre-incubation of the immunoprecipitate with the antibodies for 1 hour at 4° C. Samples of the kinase reactions were separated on SDS-PAGE, transferred to nitrocellulose membranes, visualized by autoradiography and the indicated proteins were subjected to western blot analysis.

Activation of the Canonical Pathway by CD70 is Associated with a Selective NIK-Dependent Recruitment of IKK1 to CD27:

The critical event in the canonical pathway is stimulation of the IκB-kinase activity of the IKK signalosome complex. The abilities of TNF and CD70 to activate the IKK signalosome were compared in order to examine the differences in the mechanisms of canonical pathway activation by these two ligands.

Both TNF and CD70 were found to enhance the in vitro kinase function of the IKK signalosome, manifested in phosphorylation of GST-IκBα (FIG. 5a), as well as in self-phosphorylation of the IKKs and phosphorylation of NEMO (FIG. 5b). However, whereas activation of the signalosome by TNF was not affected by NIK deficiency, the effect of CD70 on the signalosome was aborted in the NIK$^{(MINUS)}$ cells (FIGS. 5a, b).

Following activation of the signalosome by TNF all three components of the signalosome (IKK1, IKK2, and NEMO) are recruited, in about the same ratio as that found in the complex that they form in the cytosol. Signalosome recruitment to the p55 TNF receptor upon TNF treatment is induced just as effectively in NIK$^{(MINUS)}$ cells as in the wild-type cells (FIG. 5c, right panels). CD70 appears to induce the recruitment of only one of the three components of the canonical signalosome, IKK1, to CD27 and its recruitment to CD27 upon CD70 treatment is completely abolished in the NIK$^{(MINUS)}$ cells, indicating that NIK function is required for this process (FIG. 5c, left panels). Similar selective recruitment of IKK1 to CD27 upon CD70 treatment was also observed in PBMC (FIG. 5d). In the case of both the p55 TNF receptor and CD27, the kinase activity of the receptor-associated IKKs was weaker than that of the cytoplasmic signalosome (phosphorylation of GST-IκBα in top and bottom panels of FIG. 5c and also in right and left panels of FIG. 5d), suggesting that the recruitment does not result in full activation of the signalosome but merely in initiation of the activation process.

The earliest known event in activation of the signalosome by TNF is its recruitment to the p55 TNF receptor, a process facilitated by recruitment of the adapter protein RIP and TRAF2 to that receptor. CD70 does not induce recruitment of RIP to CD27, however, as shown in FIG. 6a it dose induce recruitment of TRAF2. Interestingly, the TRAF2 molecules recruited to CD27 displayed extensive electrophoretic pattern modification, probably corresponding to ubiquitination. CD70 also induced recruitment of the signalosome. Recruitment of the signalosome to the TNF receptor was prolonged, whereas association of the three components of the signalosome with CD27 could be observed only for a few minutes. At later time points the amounts of IKK2 and NEMO in the CD27 complex sharply decreased. Surprisingly, however, the amounts of IKK1 associated with the receptor remained high for a long time (FIG. 6a, left panel). Similar selective maintenance of IKK1 in association with CD27 after CD70 treatment was also observed in PBMC (FIG. 6b).

Both TNF and CD70 also induced recruitment of all three components of the canonical NF-κB complex IκBα, p65 and p50. Although p100 processing is induced by CD70 and not by TNF, recruitment of p100 to its receptor was induced by TNF but not by CD70 (FIG. 6a, right panel). This recruitment was previously suggested to occur through binding of the death domain in p100 to that in the p55 TNF receptor-associated adapter protein TRADD, and appears to serve not to activate NF-κB, but to amplify death induction by this receptor trough caspase-8 activation (Wang et al. 2002).

In NIK– cells, recruitment to the p55 TNF receptor occurred just as effectively as in the wild type cells (FIG. 6c, right panel). In contrast, recruitment of the signalosome components to CD27 was completely abolished (FIGS. 6c, d, left panels). Introduction of the wild type NIK, but not of "kinase-dead" NIK, to the NIK– cells reinstated the recruitment in response to CD70 (FIG. 6d, middle and right panels). CD70, but not TNF, also induced recruitment of NIK to its receptor. This recruitment could be observed both in cells expressing the wild type enzyme and in those that expressed its "nik-dead" mutant (FIG. 6d). Thus, while the recruitment of the signalosome components to the CD27 depends on NIK kinase function, recruitment of NIK itself to the receptor seems to occur independently of its enzymatic activity.

Example 6

Speculative Model of the Mechanisms Initiating NF-κB Activation by TNF and CD70

After comparing the initiating events in the NIK-independent activation of NF-κB by TNF and in the NIK-dependent activation by CD70 we show that the participation of NIK in activation of the canonical pathway is restricted to the effect of specific inducers.

Activation of NF-κB by the p55 TNF receptor is associated with recruitment all of the signalosome to it, and in the process the signalosome components interact with TRAF2 and RIP (Zhang et al., 2000) (Devin et al., 2000) (Devin et al., 2001). Activation of the canonical pathway by CD70, like its activation by TNF, is associated with the recruitment of the signalosome component IKK1, IKK2, and NEMO to the receptor complex. Unlike TNF, however, CD70 also induces recruitment of NIK and the signalosome components, IKK2 and NEMO to its receptor.

Recruitment of the signalosome along with NIK to CD27 is followed shortly by a sharp decrease in both IKK2 and NEMO in the receptor complex. Both IKK1 and NIK, however, remain associated with the receptor for a long time. The latter form of CD27 complex probably serves to initiate the alternative pathway (See hypothetical model in FIG. 7).

Like the recruitment of the whole signalosome to CD27, the subsequent preferential association of IKK1 with the receptor cannot be observed in cells devoid of NIK or in cells expressing non-functional NIK mutants.

Apparently, these two stages in the recruitment by CD70 are mechanistically linked, thereby ensuring that initiation of the NIK-dependent alternative activation pathway is coupled to that of the canonical pathway.

In accordance with the invention, NIK was found to bind SIVA, a protein that appears to associate with CD27 (Prasad et al., 1997). Prior art studies have shown that SIVA mediates the induction of cell death by CD27. However, death induction seems to be restricted to only one of the two known SIVA splice variants, namely SIVA1, which contains a death-domain motif (Yoon et al., 1999). We show that both SIVA2 (which lacks a death domain) and SIVA1 bind to NIK through a C-terminal region common to the two splice variants and potently enhance the activation of NF-κB by over-expressed NIK. The fact that SIVA does not enhance the activation of NF-κB by the non-functional NIK aly mutant gives credence to the possibility that SIVA plays some role in NF-κB activation by NIK. Whether this role indeed concerns the triggering of NIK function by CD27, or some other aspect of NIK function, remains to be clarified. None of the other receptors so far shown to involve NIK in their signaling is known to bind SIVA. These receptors might involve some other adapter proteins in NIK activation.

The activities mediated by the canonical and the alternative NF-κB activation pathways, though distinct, are also interrelated. The NF-κB dimers generated by the two pathways recognize different DNA sequence motifs, and thus, by affecting different promoters, can control the expression of different genes (Perkins et al., 1992) (Lin et al., 1995) (Dejardin et al., 2002) (Hoffmann et al., 2003). The two pathways also possess different kinetic features. Activation of the canonical pathway is rapid and it turns out to be transient mainly because it induces the synthesis of NF-κB-inhibitory proteins such as IκB and NF-κB2/p100. In contrast, the alternative pathway reaches effective activation only several hours following stimulation and remains active for a long time. These differences allow the two pathways to control different sets of genes, which serve different functions. Thus, consistently with their rapid induction, the dimers activated by the canonical pathway control a set of genes that mediate the early innate immune response, whereas the dimers generated by the alternative pathway control activities that contribute in a variety of ways to the prolonged and more slowly induced adaptive immune response. These differences in function correlate with the functions ascribed to the ligands that control the two activities. Pro-inflammatory cytokines such as TNF and interferon IL-1 can potently stimulate the canonical pathway, yet have little ability, if any, to stimulate the alternative one, whereas ligands such as LTα1β2, CD40L, BLyS/BAFF, and CD70, which control adaptive immunity, can, in addition to activating the canonical pathway, also effectively trigger the alternative one.

However, the mere fact that the same ligands that activate the alternative pathway also activate the canonical one allows for functional interactions between the genes regulated by these two pathways. Moreover, the two signaling pathways interact, affecting each other's activation. Induction of the canonical pathway triggers the synthesis of p100 as well as of RelB (de Wit et al., 1998) (Bren et al., 2001), which together form the precursor dimer affected by the alternative pathway, and thus potentiate the latter. Conversely, since in addition to binding to RelB p100 also associates with the dimers controlled by the canonical pathway (p65:p50 and c-Rel:p50) and thus blocks their function, its processing by the alternative pathway helps to perpetuate the activation of the canonical pathway.

To allow for coordination of the activation mechanisms for the two functionally distinct yet interacting sets of NF-κB dimers by the same inducer, they need to be controlled by both common and distinct regulatory elements. Other studies have disclosed several components unique to the alternative or to the canonical pathway. We show, for the first time, that NIK can serve as a common participant in these two distinct NF-κB-activation pathways.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES CITED

Additional References Are Cited in the Text

Akiba, H., Nakano, H., Nishinaka, S., Shindo, M., Kobata, T., Atsuta, M., Morimoto, C., Ware, C. F., Malinin, N. L., Wallach, D., et al. (1998). CD27, a member of the tumor necrosis factor receptor superfamily, activates NF-kappaB and stress-activated protein kinase/c-Jun N-terminal kinase via TRAF2, TRAF5, and NF-kappaB-inducing kinase. J Biol Chem 273, 13353-13358.

Baeuerle, P. A., and Baltimore, D. (1996). NF-kappa B: ten years after. Cell 87, 13-20.

Benjamin, D., Magrath, I. T., Maguire, R., Janus, C., Todd, H. D., and Parsons, R. G. (1982). Immunoglobulin secretion by cell lines derived from African and American undifferentiated lymphomas of Burkitt's and non-Burkitt's type. J Immunol 129, 1336-1342.

Berberich, I., Shu, G. L., and Clark, E. A. (1994). Cross-linking CD40 on B cells rapidly activates nuclear factor-kappa B. J Immunol 153, 4357-4366.

Bren, G. D., Solan, N. J., Miyoshi, H., Pennington, K. N., Pobst, L. J., and Paya, C. V. (2001). Transcription of the RelB gene is regulated by NF-kappaB. Oncogene 20, 7722-7733.

Brummelkamp, T. R., Bernards, R., and Agami, R. (2002).

A system for stable expression of short interfering RNAs in mammalian cells. Science 296, 550-553.

Camerini, D., Walz, G., Loenen, W. A., Borst, J., and Seed, B. (1991). The T cell activation antigen CD27 is a member of the nerve growth factor/tumor necrosis factor receptor gene family. J Immunol 147, 3165-3169.

Claudio, E., Brown, K., Park, S., Wang, H., and Siebenlist, U. (2002). BAFF-induced NEMO-independent processing of NF-kappa B2 in maturing B cells. Nat Immunol 3, 958-965.

Clements, G. B., Klein, G., and Povey, S. (1975). Production by EBV infection of an EBNA-positive subline from an EBNA-negative human lymphoma cell line without detectable EBV DNA. Int J Cancer 16, 125-133.

Coope, H. J., Atkinson, P. G., Huhse, B., Belich, M., Janzen, J., Holman, M. J., Klaus, G. G., Johnston, L. H., and Ley, S. C. (2002). CD40 regulates the processing of NF-kappaB2 p100 to p52. Embo J 21, 5375-5385.

de Jong, R., Loenen, W. A., Brouwer, M., van Emmerik, L., de Vries, E. F., Borst, J., and van Lier, R. A. (1991). Regulation of expression of CD27, a T cell-specific member of a novel family of membrane receptors. J Immunol 146, 2488-2494.

de Wit, H., Dokter, W. H., Koopmans, S. B., Lummen, C., van der Leij, M., Smit, J. W., and Vellenga, E. (1998). Regulation of p100 (NFKB2) expression in human monocytes in response to inflammatory mediators and lymphokines. Leukemia 12, 363-370.

Dejardin, E., Droin, N. M., Delhase, M., Haas, E., Cao, Y., Makris, C., Li, Z. W., Karin, M., Ware, C. F., and Green, D. R. (2002). The lymphotoxin-beta receptor induces different patterns of gene expression via two NF-kappaB pathways. Immunity 17, 525-535.

Derudder, E., Dejardin, E., Pritchard, L. L., Green, D. R., Korner, M., and Baud, V. (2003). RelB/p50 dimers are differentially regulated by tumor necrosis factor-alpha and lymphotoxin-beta receptor activation: critical roles for p100. J Biol Chem 278, 23278-23284.

Devin, A., Cook, A., Lin, Y., Rodriguez, Y., Kelliher, M., and Liu, Z. (2000). The distinct roles of TRAF2 and RIP in IKK activation by TNF-R1: TRAF2 recruits IKK to TNF-R1 while RIP mediates IKK activation. Immunity 12, 419-429.

Devin, A., Lin, Y., Yamaoka, S., Li, Z., Karin, M., and Liu, Z. (2001). The alpha and beta subunits of IkappaB kinase (IKK) mediate TRAF2-dependent IKK recruitment to tumor necrosis factor (TNF) receptor 1 in response to TNF. Mol Cell Biol 21, 3986-3994.

Erlichman, B., and Howard, O. M. (1999). CD27 signals through PKC in human B cell lymphomas. Cytokine 11, 476-484.

Fagarasan, S., Shinkura, R., Kamata, T., Nogaki, F., Ikuta, K., Tashiro, K., and Honjo, T. (2000). Alymphoplasia (aly)-type nuclear factor kappaB-inducing kinase (NIK) causes defects in secondary lymphoid tissue chemokine receptor signaling and homing of peritoneal cells to the gut-associated lymphatic tissue system. J Exp Med 191, 1477-1486.

Fanslow, W. C., Clifford, K. N., Seaman, M., Alderson, M. R., Spriggs, M. K., Armitage, R. J., and Ramsdell, F. (1994). Recombinant CD40 ligand exerts potent biologic effects on T cells. J Immunol 152, 4262-4269.

Ghosh, S., and Karin, M. (2002). Missing pieces in the NF-kappaB puzzle. Cell 109 Suppl, S81-96.

Ghosh, S., May, M. J., and Kopp, E. B. (1998). NF-kappa B and Rel proteins: evolutionarily conserved mediators of immune responses. Annu Rev Immunol 16, 225-260.

Hannink, M., and Temin, H. M. (1990). Structure and autoregulation of the c-rel promoter. Oncogene 5, 1843-1850.

Hatada, E. N., Do, R. K., Orlofsky, A., Liou, H. C., Prystowsky, M., MacLennan, I. C., Caamano, J., and Chen-Kiang, S. (2003). NF-kappaB1 p50 is required for BLyS attenuation of apoptosis but dispensable for processing of NF-kappaB2 p100 to p52 in quiescent mature B cells. J Immunol 171, 761-768.

Hintzen, R. Q., Lens, S. M., Beckmann, M. P., Goodwin, R. G., Lynch, D., and van Lier, R. A. (1994). Characterization of the human CD27 ligand, a novel member of the TNF gene family. J Immunol 152, 1762-1773.

Hoffmann, A., Leung, T. H., and Baltimore, D. (2003). Genetic analysis of NF-kappaB/Rel transcription factors defines functional specificities. Embo J 22, 5530-5539.

Karin, M., and Ben-Neriah, Y. (2000). Phosphorylation meets ubiquitination: the control of NF-[kappa]B activity. Annu Rev Immunol 18, 621-663.

Karrer, U., Althage, A., Odermatt, B., Hengartner, H., and Zinkernagel, R. M. (2000). Immunodeficiency of alymphoplasia mice (aly/aly) in vivo: structural defect of secondary lymphoid organs and functional B cell defect. Eur J Immunol 30, 2799-2807.

Kayagaki, N., Yan, M., Seshasayee, D., Wang, H., Lee, W., French, D. M., Grewal, I. S., Cochran, A. G., Gordon, N. C., Yin, J., et al. (2002). BAFF/BLyS receptor 3 binds the B cell survival factor BAFF ligand through a discrete surface loop and promotes processing of NF-kappaB2. Immunity 17, 515-524.

Leonardi, A., Vito, P., Mauro, C., Pacifico, F., Ulianich, L., Consiglio, E., Formisano, S., and Di Jeso, B. (2002). Endoplasmic reticulum stress causes thyroglobulin retention in this organelle and triggers activation of nuclear factor-kappa B via tumor necrosis factor receptor-associated factor 2. Endocrinology 143, 2169-2177.

Lin, R., Gewert, D., and Hiscott, J. (1995). Differential transcriptional activation in vitro by NF-kappa B/Rel proteins. J Biol Chem 270, 3123-3131.

Lin, X., Mu, Y., Cunningham, E. T., Jr., Marcu, K. B., Geleziunas, R., and Greene, W. C. (1998). Molecular determinants of NF-kappaB-inducing kinase action. Mol Cell Biol 18, 5899-5907.

Ling, L., Cao, Z., and Goeddel, D. V. (1998). NF-kappaB-inducing kinase activates IKK-alpha by phosphorylation of Ser-176. Proc Natl Acad Sci USA 95, 3792-3797.

Locksley, R. M., Killeen, N., and Lenardo, M. J. (2001). The TNF and TNF receptor superfamilies: integrating mammalian biology. Cell 104, 487-501.

Lois, C., Hong, E. J., Pease, S., Brown, E. J., and Baltimore, D. (2002). Germline transmission and tissue-specific expression of transgenes delivered by lentiviral vectors. Science 295, 868-872.

Lombardi, L., Ciana, P., Cappellini, C., Trecca, D., Guerrini, L., Migliazza, A., Maiolo, A. T., and Neri, A. (1995). Structural and functional characterization of the promoter regions of the NFKB2 gene. Nucleic Acids Res 23, 2328-2336.

Malinin, N. L., Boldin, M. P., Kovalenko, A. V., and Wallach, D. (1997). MAP3K-related kinase involved in NF-kappaB induction by TNF, CD95 and IL-1. Nature 385, 540-544.

Matsumoto, M., Iwamasa, K., Rennert, P. D., Yamada, T., Suzuki, R., Matsushima, A., Okabe, M., Fujita, S., and Yokoyama, M. (1999). Involvement of distinct cellular compartments in the abnormal lymphoid organogenesis in lymphotoxin-alpha-deficient mice and alymphoplasia (aly) mice defined by the chimeric analysis. J Immunol 163, 1584-1591.

Matsushima, A., Kaisho, T., Rennert, P. D., Nakano, H., Kurosawa, K., Uchida, D., Takeda, K., Akira, S., and Matsumoto, M. (2001). Essential role of nuclear factor (NF)-kappaB-inducing kinase and inhibitor of kappaB (IkappaB) kinase alpha in NF-kappaB activation through lymphotoxin beta receptor, but not through tumor necrosis factor receptor I. J Exp Med 193, 631-636.

Miyawaki, S., Nakamura, Y., Suzuka, H., Koba, M., Yasumizu, R., Ikehara, S., and Shibata, Y. (1994). A new mutation, aly, that induces a generalized lack of lymph nodes accompanied by immunodeficiency in mice. Eur J Immunol 24, 429-434.

O'Mahony, A., Lin, X., Geleziunas, R., and Greene, W. C. (2000). Activation of the heterodimeric IkappaB kinase alpha (IKKalpha)-IKKbeta complex is directional: IKKalpha regulates IKKbeta under both basal and stimulated conditions. Mol Cell Biol 20, 1170-1178.

Pahl, H. L., and Baeuerle, P. A. (1996). Activation of NF-kappa B by ER stress requires both Ca2+ and reactive oxygen intermediates as messengers. FEBS Lett 392, 129-136.

Perkins, N. D., Schmid, R. M., Duckett, C. S., Leung, K., Rice, N. R., and Nabel, G. J. (1992). Distinct combinations of NF-kappa B subunits determine the specificity of transcriptional activation. Proc Natl Acad Sci USA 89, 1529-1533.

Pomerantz, J. L., and Baltimore, D. (2002). Two pathways to NF-kappaB. Mol Cell 10, 693-695.

Prasad, K. V., Ao, Z., Yoon, Y., Wu, M. X., Rizk, M., Jacquot, S., and Schlossman, S. F. (1997). CD27, a member of the tumor necrosis factor receptor family, induces apoptosis and binds to Siva, a proapoptotic protein. Proc Natl Acad Sci USA 94, 6346-6351.

Pulvertaft, J. V. (1964). Cytology of Burkitt's Tumour (African Lymphoma). Lancet 39, 238-240.

Regnier, C. H., Song, H. Y., Gao, X., Goeddel, D. V., Cao, Z., and Rothe, M. (1997). Identification and characterization of an IkappaB kinase. Cell 90, 373-383.

Sambrook, J., Fritsch, E., and Maniatis, T. (1989). Molecular cloning. A laboratory manual., Vol 1, 2nd edn (Cold Spring Harbor, N.Y., Cold Spring Harbor Laboratory Press).

Schreiber, E., Matthias, P., Muller, M. M., and Schaffner, W. (1989). Rapid detection of octamer binding proteins with 'mini-extracts', prepared from a small number of cells. Nucleic Acids Res 17, 6419.

Sen, R., and Baltimore, D. (1986). Inducibility of kappa immunoglobulin enhancer-binding protein Nf-kappa B by a posttranslational mechanism. Cell 47, 921-928.

Senftleben, U., Cao, Y., Xiao, G., Greten, F. R., Krahn, G., Bonizzi, G., Chen, Y., Hu, Y., Fong, A., Sun, S. C., and Karin, M. (2001). Activation by IKKalpha of a second, evolutionary conserved, NF-kappa B signaling pathway. Science 293, 1495-1499.

Shinkura, R., Kitada, K., Matsuda, F., Tashiro, K., Ikuta, K., Suzuki, M., Kogishi, K., Serikawa, T., and Honjo, T. (1999). Alymphoplasia is caused by a point mutation in the mouse gene encoding Nf-kappa b-inducing kinase. Nat Genet 22, 74-77.

Solan, N. J., Miyoshi, H., Carmona, E. M., Bren, G. D., and Paya, C. V. (2002). RelB cellular regulation and transcriptional activity are regulated by p100. J Biol Chem 277, 1405-1418.

Song, H. Y., Regnier, C. H., Kirschning, C. J., Goeddel, D. V., and Rothe, M. (1997). Tumor necrosis factor (TNF)-mediated kinase cascades: bifurcation of nuclear factor-kappaB and c-jun N-terminal kinase (JNK/SAPK) pathways at TNF receptor-associated factor 2. Proc Natl Acad Sci USA 94, 9792-9796.

Ten, R. M., Paya, C. V., Israel, N., Le Bail, O., Mattei, M. G., Virelizier, J. L., Kourilsky, P., and Israel, A. (1992). The characterization of the promoter of the gene encoding the p50 subunit of NF-kappa B indicates that it participates in its own regulation. Embo J 11, 195-203.

Thompson, J. S., Bixler, S. A., Qian, F., Vora, K., Scott, M. L., Cachero, T. G., Hession, C., Schneider, P., Sizing, I. D., Mullen, C., et al. (2001). BAFF-R, a newly identified TNF receptor that specifically interacts with BAFF. Science 293, 2108-2111.

Ueberla, K., Lu, Y., Chung, E., and Haseltine, W. A. (1993). The NF-kappa B p65 promoter. J Acquir Immune Defic Syndr 6, 227-230.

Uhlik, M., Good, L., Xiao, G., Harhaj, E. W., Zandi, E., Karin, M., and Sun, S. C. (1998). NF-kappaB-inducing kinase and IkappaB kinase participate in human T-cell leukemia virus I Tax-mediated NF-kappaB activation. J Biol Chem 273, 21132-21136.

Wallach, D., Varfolomeev, E. E., Malinin, N. L., Goltsev, Y. V., Kovalenko, A. V., and Boldin, M. P. (1999). Tumor necrosis factor receptor and Fas signaling mechanisms. Annu Rev Immunol 17, 331-367.

Xiao, G., Harhaj, E. W., and Sun, S. C. (2001). NF-kappaB-inducing kinase regulates the processing of NF-kappaB2 p100. Mol Cell 7, 401-409.

Xiao, G., and Sun, S. C. (2000). Negative regulation of the nuclear factor kappa B-inducing kinase by a cis-acting domain. J Biol Chem 275, 21081-21085.

Yamada, T., Mitani, T., Yorita, K., Uchida, D., Matsushima, A., Iwamasa, K., Fujita, S., and Matsumoto, M. (2000). Abnormal immune function of hemopoietic cells from alymphoplasia (aly) mice, a natural strain with mutant NF-kappa B-inducing kinase. J Immunol 165, 804-812.

Yamamoto, H., Kishimoto, T., and Minamoto, S. (1998). NF-kappaB activation in CD27 signaling: involvement of TNF receptor-associated factors in its signaling and identification of functional region of CD27. J Immunol 161, 4753-4759.

Yan, M., Brady, J. R., Chan, B., Lee, W. P., Hsu, B., Harless, S., Cancro, M., Grewal, I. S., and Dixit, V. M. (2001). Identification of a novel receptor for B lymphocyte stimulator that is mutated in a mouse strain with severe B cell deficiency. Curr Biol 11, 1547-1552.

Yilmaz, Z. B., Weih, D. S., Sivakumar, V., and Weih, F. (2003). RelB is required for Peyer's patch development: differential regulation of p52-RelB by lymphotoxin and TNF. Embo J 22, 121-130.

Yin, L., Wu, L., Wesche, H., Arthur, C. D., White, J. M., Goeddel, D. V., and Schreiber, R. D. (2001). Defective lymphotoxin-beta receptor-induced NF-kappaB transcriptional activity in NIK$^{(MINUS)}$ deficient mice. Science 291, 2162-2165.

Yoon, Y., Ao, Z., Cheng, Y., Schlossman, S. F., and Prasad, K. V. (1999). Murine Siva-1 and Siva-2, alternate splice forms of the mouse Siva gene, both bind to CD27 but differentially transduce apoptosis. Oncogene 18, 7174-7179.

Zhang, S. Q., Kovalenko, A., Cantarella, G., and Wallach, D. (2000). Recruitment of the IKK signalosome to the p55 TNF receptor: RIP and A20 bind to NEMO (IKKgamma) upon receptor stimulation. Immunity 12, 301-311.

What is claimed is:

1. A method of treating an immune disorder, said method comprising administering to an individual having the immune disorder a therapeutically effective amount of an agent capable of decreasing NF-κB inducing kinase (NIK)-SIVA complex formation, thereby treating the immune disorder in the individual, wherein said agent is (i) an antibody capable of binding to the amino acid sequence at amino acid residues 123-175 of SEQ ID NO:3 (SIVA1), or (ii) an antibody capable of binding to the amino acid sequence at amino acid residues 58-110 of SEQ ID NO:4 (SIVA2).

2. The method according to claim 1, wherein said immune disorder is characterized by abnormal function or level of at least one protein selected from the group consisting of B lymphocyte stimulator protein (BLyS)/BAFF, CD27, SIVA and NIK.

3. The method according to claim 1, wherein said immune disorder is selected from the group consisting of multiple myeloma (MM), acquired immunodeficiency syndrome (AIDs), Sjogren's syndrome (SS), B-cells chronic lymphocytic leukemia (B-CLL), systemic lupus erythematosus, inflammatory colon disease, systemic inflammatory response syndrome (SIRS), multiple organ disinfection syndrome (MODS) and acute respiratory distress syndrome (ARDS).

* * * * *